United States Patent
Nguyen

(10) Patent No.: US 9,522,057 B2
(45) Date of Patent: Dec. 20, 2016

(54) DELIVERY SYSTEMS FOR THE PLACEMENT OF SURGICAL IMPLANTS AND METHODS OF USE

(71) Applicant: Ethicon, Inc., Somerville, NJ (US)

(72) Inventor: Steven H. Nguyen, North Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 506 days.

(21) Appl. No.: 13/827,564

(22) Filed: Mar. 14, 2013

(65) Prior Publication Data

US 2014/0276994 A1    Sep. 18, 2014

(51) Int. Cl.
*A61F 2/02* (2006.01)
*A61F 2/00* (2006.01)

(52) U.S. Cl.
CPC ........... *A61F 2/0063* (2013.01); *A61F 2/0045* (2013.01); *A61F 2220/0033* (2013.01)

(58) Field of Classification Search
CPC ............ A61F 2/0063; A61F 2220/0033; A61F 2/0045
USPC ....... 600/29–32, 37; 606/151; 128/834, 885, 128/897–899
See application file for complete search history.

(56) References Cited

U.S. PATENT DOCUMENTS

2008/0015618 A1* 1/2008 Sonnenschein et al. ..... 606/157
2009/0221867 A1* 9/2009 Ogdahl et al. ................. 600/37
2009/0281556 A1* 11/2009 Newell et al. ................ 606/144
2010/0234681 A1* 9/2010 Knapp et al. .................... 600/37
2010/0312357 A1* 12/2010 Levin et al. ................ 623/23.72
2011/0034759 A1* 2/2011 Ogdahl et al. ................... 600/37
2012/0316386 A1* 12/2012 Wirbisky et al. ................ 600/30
2014/0343579 A1* 11/2014 Viker et al. .................... 606/151

FOREIGN PATENT DOCUMENTS

WO    WO 02/058562    8/2002
WO    WO 2007/059368    5/2007

OTHER PUBLICATIONS

Written Opinion of the International Search Authority for International Application No. PCT/US2014/020457, 6 pages.

* cited by examiner

*Primary Examiner* — Navin Natnithithadha
*Assistant Examiner* — Sunita Reddy

(57) ABSTRACT

An implant insertion system includes an implant, such as a surgical mesh, having a first end and a second end, a first insertion aid spaced from and connected with the first end of the implant via a first link, such as a first flexible filament, and a second insertion aid spaced from and connected with the second end of the implant via a second link, such as a second flexible filament. The system includes an insertion device for implanting the implant in tissue. The insertion device has a handle at a proximal end thereof, an actuator mounted on the handle, a shaft extending from a distal end of the handle toward a distal end of the insertion device, and a cutting element disposed within the shaft. The shaft has an outer wall including an opening that is adapted to receive the first and second insertion aids for connecting the implant with the insertion device. The actuator is engageable for moving the cutting element from a first position to a second position for severing one of the links for breaking the connection between one of the first and second insertion aids and the surgical implant.

25 Claims, 25 Drawing Sheets

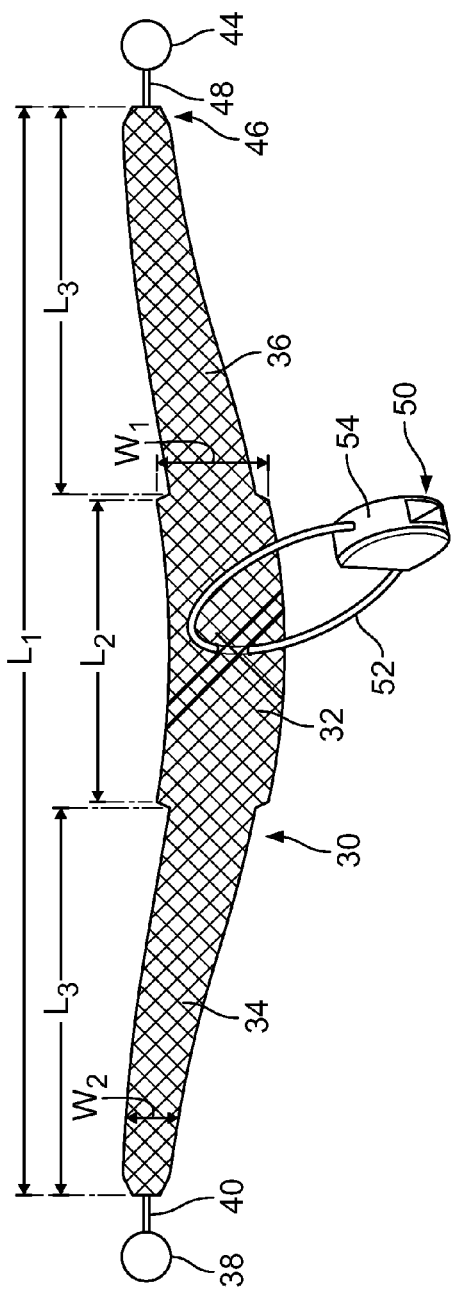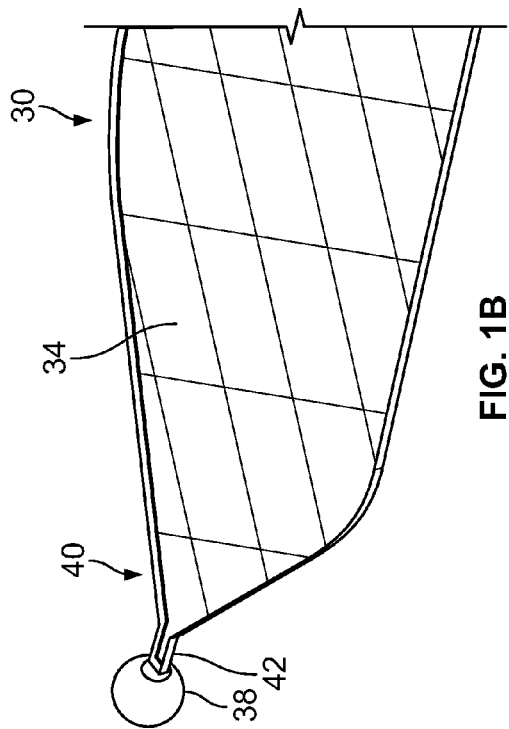
FIG. 1A
FIG. 1B

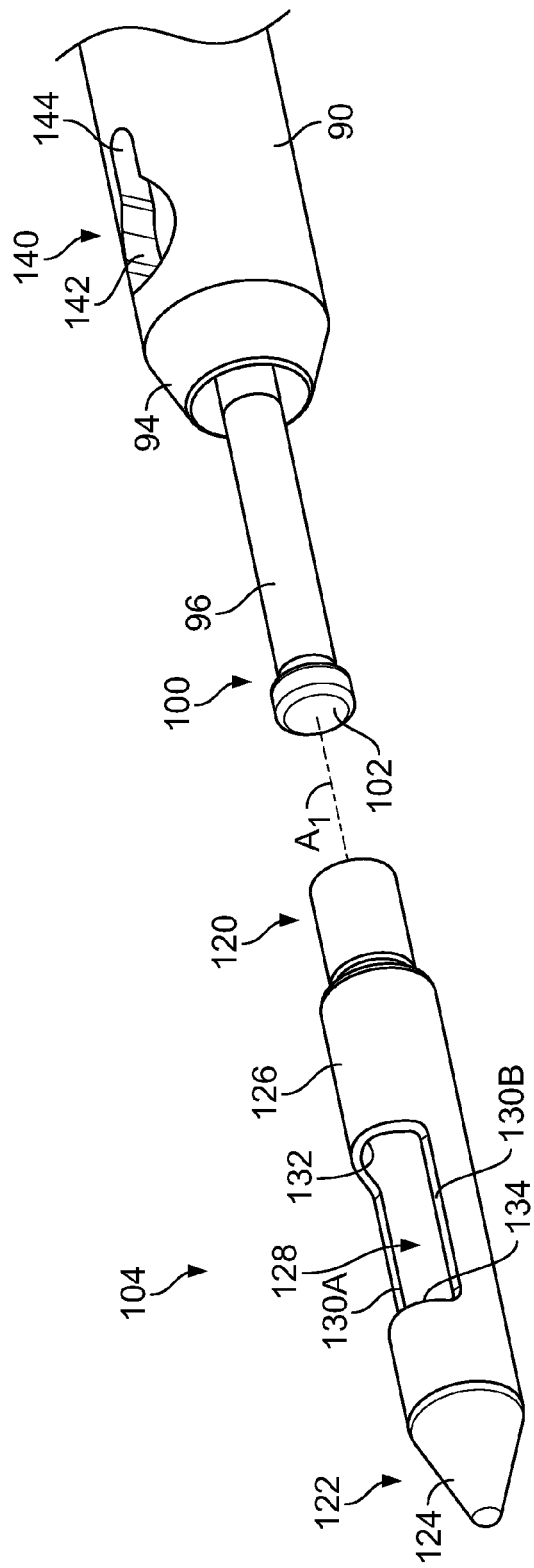
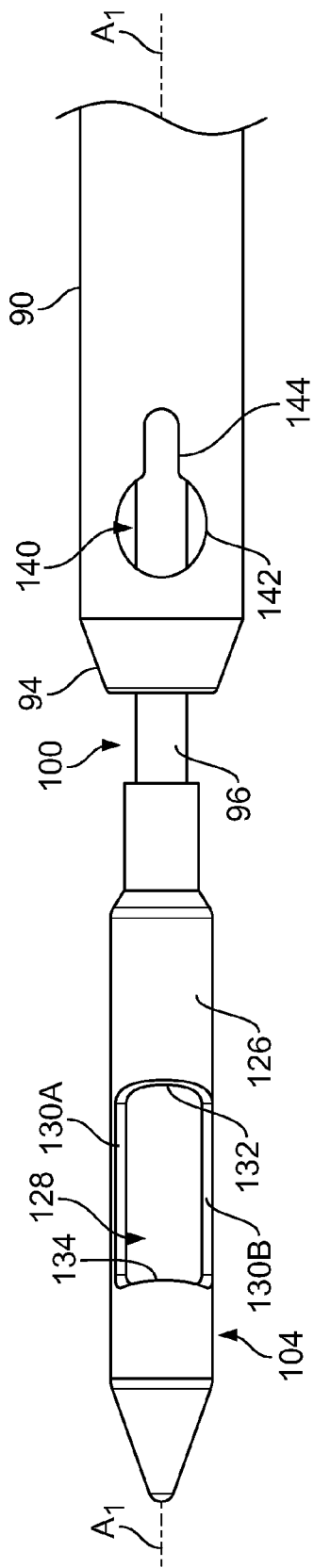
FIG. 5A
FIG. 5B

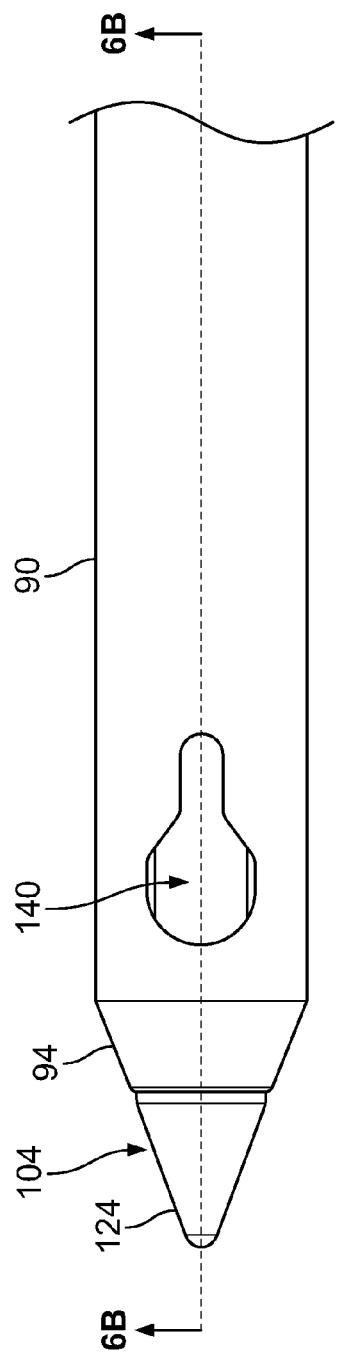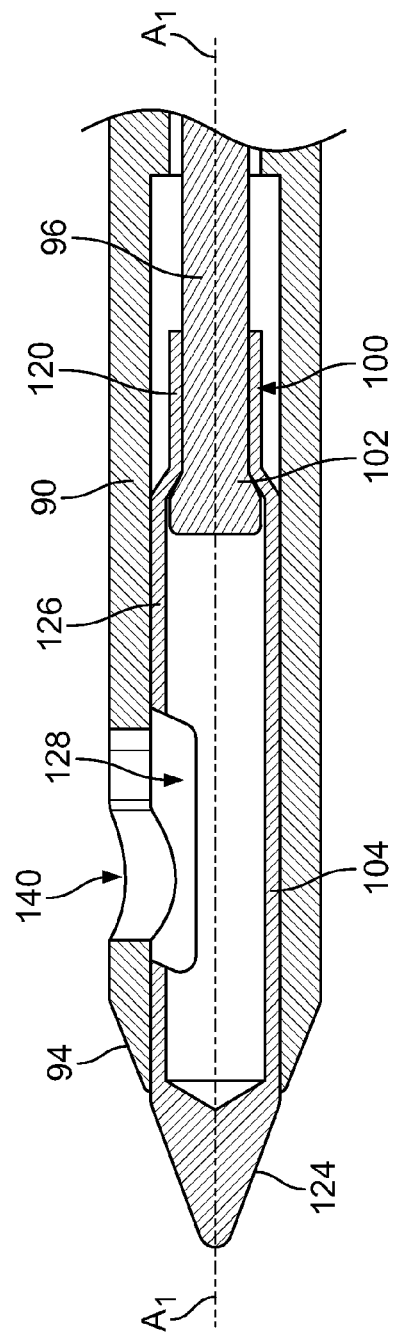
FIG. 6A
FIG. 6B

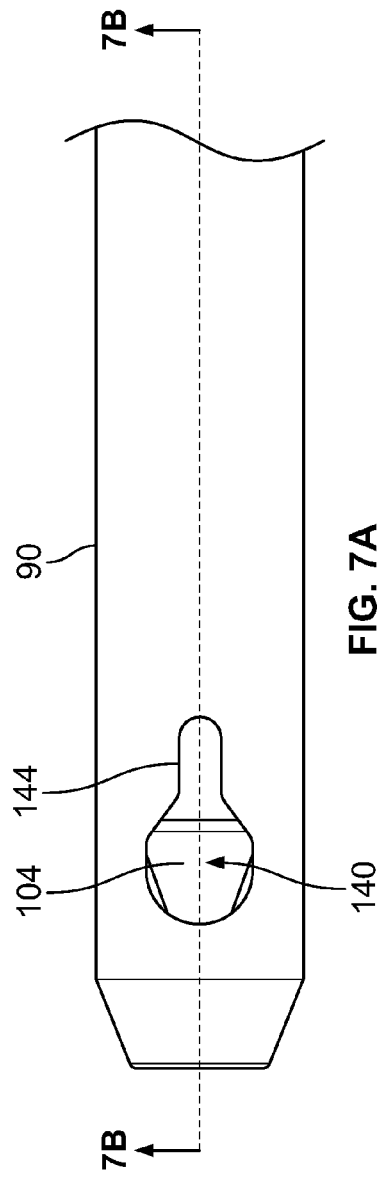
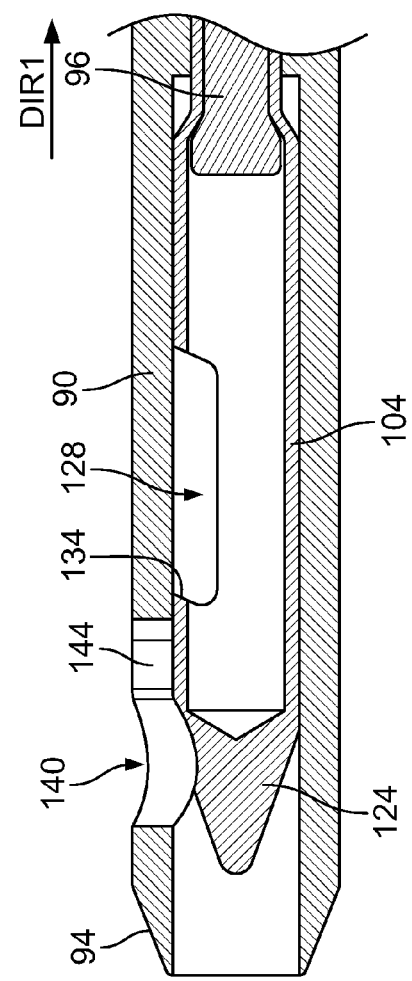
FIG. 7A
FIG. 7B

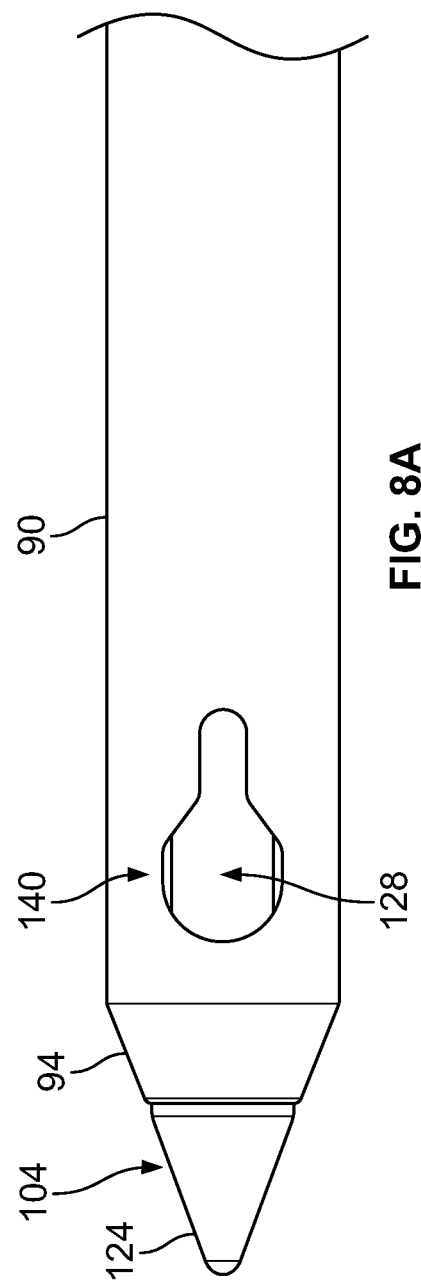

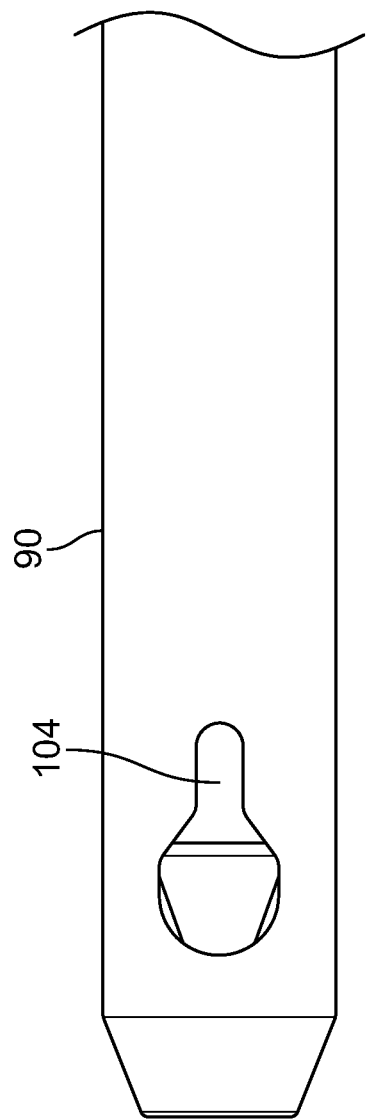

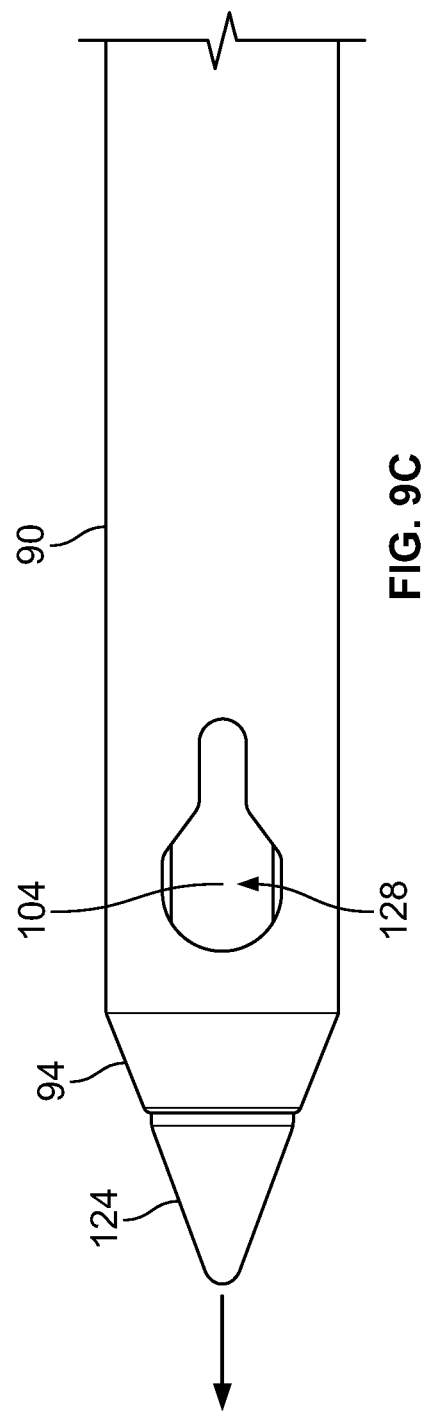

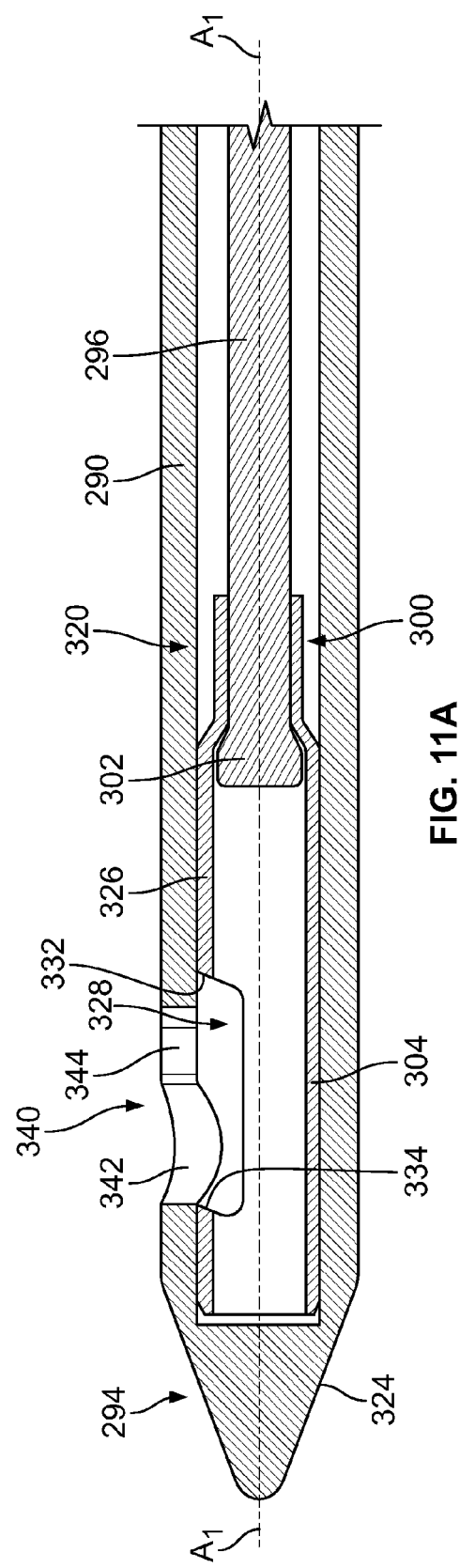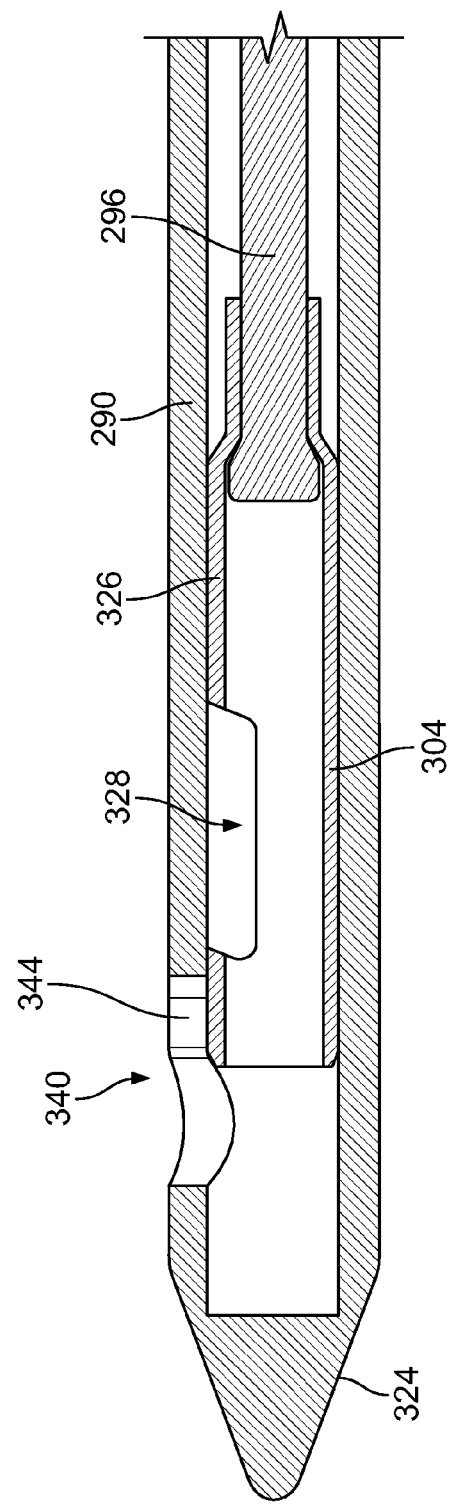

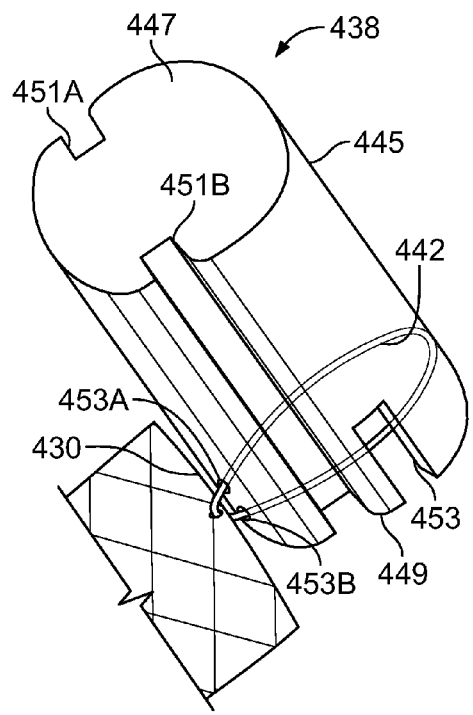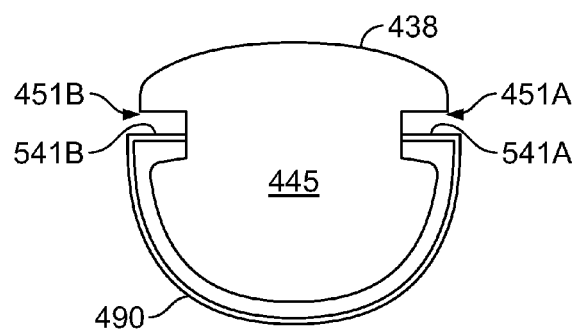
FIG. 13C  FIG. 13D
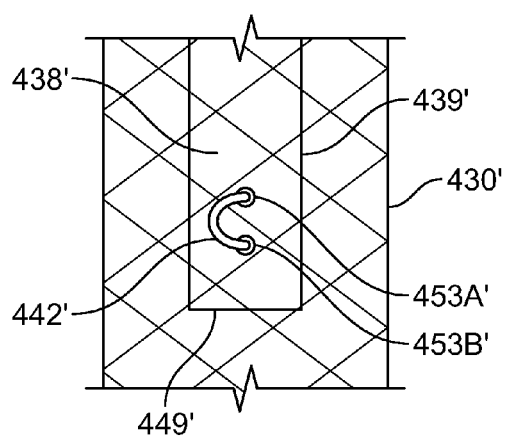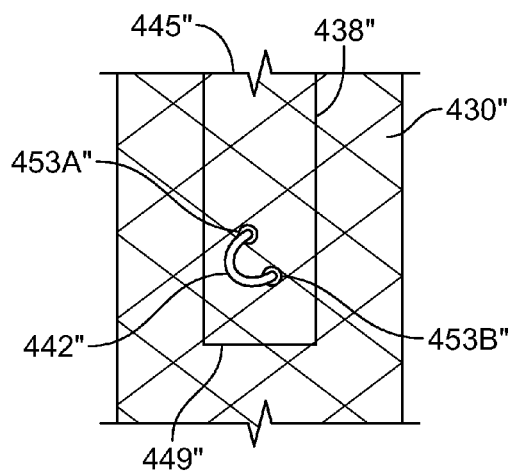
FIG. 14  FIG. 15

DELIVERY SYSTEMS FOR THE PLACEMENT OF SURGICAL IMPLANTS AND METHODS OF USE

BACKGROUND OF THE INVENTION

Field of the Invention

The present invention generally relates to systems, devices and methods for inserting biomedical implants, and more particularly, to systems, devices and methods for accurately positioning biomedical implants in tissue.

Description of the Related Art

Women account for more than 11 million incontinence cases, with many of those women suffering from stress urinary incontinence (SUI). Women with SUI involuntarily lose urine during normal daily activities and movements, such as laughing, coughing, sneezing and regular exercise.

SUI may be caused by a functional defect or weakened tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle and shy away from social situations.

One device and method for treating female urinary stress incontinence is described in detail in U.S. Pat. No. 5,899,909, which is incorporated herein by reference in its entirety. The '909 patent discloses a surgical instrument comprising a shank having a handle at one end and connecting means at the other end to receive, one at a time, two curved needle-like elements which each are connected at one end to respective ends of a mesh intended to be implanted into the body. In practice, the mesh is passed into the body via the vagina first at one end and then at the other end, at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by Ethicon Inc., a Johnson & Johnson Company, of Somerville, N.J., USA. In this procedure two 5 mm needles pass a PROLENE mesh trans-vaginally and through the abdomen to create a tension-free support under the mid-urethra.

Sub-urethral slings have also been placed by a different approach wherein a needle is passed first though the abdominal wall along the same path as described above, and eventually exiting through the vaginal incision. The tape is then coupled to the needle in some manner, and pulled back through the body from the vaginal incision and out through the abdominal incision. The chosen approach, vaginal or abdominal, will often depend on the preferences of the surgeon.

Yet another approach for implanting a sub-urethral sling has also been recently developed in which the implanted sling extends from beneath the urethra, and out through the obturator hole on either side. This "transobturator" procedure may involve inserting an appropriately configured needle from a vaginal incision and subsequently out through the obturator hole, or vice versa. The former technique (an "inside-out" approach) and associated instruments are described in detail in U.S. Pat. Nos. 7,611,454, 7,204,802, and 7,261,723, and U.S. Patent Publication No. 2009/0306459, which are incorporated herein by reference in their entirety. As illustrated in U.S. Pat. No. 7,261,723, this technique may be performed using a surgical instrument including a surgical passer or introducer and tube elements applied over the ends of the surgical passers that are coupled to the tape to be implanted under the urethra.

More recently, sub-urethral slings that do not exit the body through the abdominal wall or the buttocks have been developed. These sub-urethral slings are secured inside the body into bone, tissue or the like. One embodiment is described in U.S. Pat. No. 7,285,086, the disclosure of which is hereby incorporated by reference herein.

With sub-urethral slings, proper and accurate positioning of the distal ends within targeted tissue is essential in order to have and maintain the proper amount of support under the urethra to alleviate incontinence. One challenge encountered in achieving this is that the ends of the sling must be coupled to some type of insertion device to be placed in position, then subsequently uncoupled from the insertion device so that the insertion device can be withdrawn leaving the implant in place within the body. Many insertion devices for coupling an implant to the insertion device, however, have no attachment mechanisms, have cumbersome attachment mechanisms, and/or require undesirable forces to be applied to uncouple the implant, which, in turn, frequently moves or dislodges the ends of the implant from the targeted and desired position upon uncoupling.

In one embodiment, commonly assigned U.S. patent application Ser. No. 13/488,664, filed Jun. 5, 2012, now U.S. Pat. No. 9,044,223, the disclosure of which is hereby incorporated by reference herein, teaches an implant insertion system including an implant, such as a surgical mesh, having at least one insertion tip secured to the implant. Each insertion tip has a tapered distal end, a proximal end, a base extending proximally from the tapered distal end, and a central lumen formed in the base having an opening facing the proximal end of the insertion tip. The system includes an insertion device having an outer shaft and a latching assembly provided at a distal end of the outer shaft that is insertable into the opening of the central lumen for selectively locking the insertion tip to the latching assembly. The latching assembly has an outer dimension that is changeable from an expanded state for locking the insertion tip to the latching assembly to a non-expanded state for unlocking the insertion tip from the latching assembly.

In spite of the above advances, there remains a need for additional delivery systems for implanting surgical mesh implants whereby the insertion aids used for advancing the surgical mesh through tissue may be removed from the patient after use.

SUMMARY OF THE INVENTION

In one embodiment, an implant insertion system includes an implant, such as a surgical mesh or hemostat patch, having at least one insertion aid secured to at least one end of the implant. In one embodiment, the implant has a first end and a second end, a first insertion aid connected with the first end of the implant, and a second insertion aid connected with the second end of the implant. In one embodiment, only one insertion aid may be attached to an implant. In one embodiment, three of more insertion aids may be attached to an implant. The insertion aids are preferably removable from being connected with the implant. In one embodiment, the implant is a surgical mesh that is made of a first material, and the first and second insertion aids are made of a second material that is different than the first material.

In one embodiment, the implant insertion system desirably includes an insertion device having a handle, an actuator, an elongated shaft extending from the handle, and a cutting element disposed within the elongated shaft. In one embodiment, the elongated shaft preferably has an outer wall including an opening that is adapted to receive one of the first and second insertion aids for connecting the implant with the insertion device. The actuator is engageable for moving the cutting element from a first position (e.g., an extended position) to a second position (e.g., a retracted position) for breaking the connection between one of the first and second insertion aids and the implant.

In one embodiment, the implant insertion system desirably includes a first link connecting the first insertion aid with the first end of the implant, and a second link connecting the second insertion aid with the second end of the implant. In one embodiment, the cutting element contacts the first and second link when moving between the first and second positions for separating the first and second insertion aids from the surgical implant. In one embodiment, the first and second links are flexible filaments that extend between the first and second insertion aids and the respective first and second ends of the implant. In one embodiment, the first and second links are desirably threads that pass through pores of a surgical mesh implant and that are wrapped around the first and second insertion aids.

The first and second insertion aids may have various geometric shapes such as spheres, circles, squares, rectangles, tubes, cubes, parallelograms, and combinations thereof.

In one embodiment, the opening in the outer wall of the shaft for receiving the insertion aids is located at a distal end of the elongated shaft. The opening at the distal end of the elongated shaft preferably has a keyhole shape with a wider distal section and a narrower proximal section. In one embodiment, the insertion aid has a diameter that is smaller than the size of the wider distal section of the keyhole opening and larger than the size of the narrower proximal section of the keyhole opening.

In one embodiment, the cutting element has a distal end with a pointed tip that helps the distal end of the elongated shaft of the insertion device to advance through tissue. In one embodiment, the pointed tip projects beyond the distal end of the elongated shaft when the cutting element is in the first position and is proximal to the distal end of the elongated shaft when the cutting element is in the second position. In one embodiment, the pointed tip for advancing the insertion device through tissue is provided on the elongated shaft and is located at the distal-most end of the elongated shaft.

In one embodiment, an implant insertion system for implanting an implant in tissue preferably includes an implant having a first end and a second end, a first insertion aid spaced from and connected with the first end of the implant via a first link, and a second insertion aid spaced from and connected with the second end of the implant via a second link. The implant insertion system desirably includes an insertion device for implanting the implant in tissue, the insertion device including a handle at a proximal end thereof, an actuator mounted on the handle, a shaft extending from a distal end of the handle toward a distal end of the insertion device, and a cutting element disposed within the shaft. The shaft preferably has an outer wall including an opening that is adapted to receive the first and second insertion aids for connecting the implant with the insertion device. The actuator is engageable for moving the cutting element from a first position to a second position for severing one of the links for breaking the connection between one of the first and second insertion aids and the surgical implant.

In one embodiment, the insertion device has a longitudinal axis, and the cutting element is preferably adapted to move along the longitudinal axis between the first position and the second position. In one embodiment, the cutting element moves proximally along the longitudinal axis of the insertion device to sever the insertion aid from the implant. In one embodiment, the cutting element moves distally along the longitudinal axis of the insertion device to sever the insertion aid from the implant. In one embodiment, in addition to the axial movement, the insertion aid may also rotate about the longitudinal axis of the insertion device to sever the insertion aid from the implant. In one embodiment, the cutting element may only rotate to sever the insertion aids from the implant. In one embodiment, the cutting element includes a cutting edge having a shape that is selected from the group consisting of a straight cutting edge, a circular cutting edge, and a half-moon cutting edge.

In one embodiment, the insertion device is a single cut device that is used to make only one cut during a surgical procedure. In one embodiment, the insertion device may be used to make multiple cuts whereby two or more insertion aids are severed from their connection with one or more implants. In one embodiment, when the insertion aids are severed, the insertion aids remain within the shaft of the insertion device for being removed from the body as the insertion device is retracted from the patient.

In one embodiment, the insertion device preferably includes the shaft having an elongated conduit extending from a proximal end to a distal end of the shaft, an actuating wire disposed within the elongated conduit of the shaft and adapted to move in proximal and distal directions relative to the shaft, the cutting element being connected with a distal end of the actuating wire; and the actuator being connected with a proximal end of the actuating wire, whereby the actuator is pushed toward the distal end of the shaft for moving the cutting element between the first position and the second position.

In one embodiment, the cutting element preferably includes a tubular body having a proximal end connected with the distal end of the actuating wire. The tubular body desirably has a window formed in an outer wall thereof that is in axial alignment with the opening in the outer wall of the shaft when the cutting element is in the first position, and is not in alignment with the opening in the outer wall of the shaft when the cutting element is in the second position.

In one embodiment, when the cutting element is in the first position, the insertion aid is insertable through the aligned opening in the outer wall of the shaft and the window formed in the tubular body of the cutting element.

In one embodiment, the shaft is made of metal. In one embodiment, the cutting element is made of metal. In one embodiment, the handle for the insertion device is made of polymer materials. In one embodiment, the implant is a surgical mesh or a mesh and suture combination. In one embodiment, the insertion aid is made of a polymer material. In one embodiment, the actuating wire is flexible and may be made of stainless steel, polymers, nylon, Teflon, polypropylene and combinations thereof.

In one embodiment, the insertion aids are severed from the implant by moving the actuator toward the distal end of the handle, which, in turn, rotates a cam element mounted within the handle in a counterclockwise direction, which, in turn, pulls the actuating wire proximally for moving the cutting element proximally from the first position to the second position.

In one embodiment, the implant insertion system preferably includes a left-hand insertion device for engaging a first insertion aid connected with a first end of an implant, and a right-hand insertion device for engaging a second insertion aid connected with a second end of the implant.

In one embodiment, a method of implanting a surgical mesh in tissue preferably includes providing a surgical mesh having a first end and a second end, a first insertion aid connected with the first end of the surgical mesh, and a second insertion aid connected with the second end of the surgical mesh, providing an insertion device including a handle, an actuator, an elongated shaft extending from the handle, and a cutting element disposed at a distal end of the elongated shaft, the elongated shaft having an outer wall including an opening at the distal end of the elongated shaft that is adapted to receive at least one of the first and second insertion aids.

In one embodiment, the method desirably includes inserting one of the insertion aids into the opening at the distal end of the elongated shaft for connecting the surgical mesh with the insertion device, forming a surgical opening in tissue, after inserting one of the insertion aids into the opening, advancing the distal end of the elongated shaft and the surgical mesh connected with the insertion device through the surgical opening until the one of the insertion aids and the end of the surgical mesh connected with the one of the insertion aids are disposed at a first location within the tissue, and engaging the actuator for moving the cutting element from a first position to a second position for severing the one of the insertion aids from one of the ends of the surgical mesh.

In one embodiment, the method desirably includes, after severing the one of the insertion aids, removing the elongated shaft from the tissue while leaving the severed end of one of the ends of the surgical mesh within the tissue, releasing the actuator for moving the cutting element from the second position back to the first position, and inserting the other one of the insertion aids into the opening at the distal end of the elongated shaft for connecting the other end of the surgical mesh with the insertion device. The method preferably includes, after inserting the other one of the insertion aids into the opening, advancing the distal end of the elongated shaft and the other end of the surgical mesh connected with the insertion device through tissue until the other one of the insertion aids and the other end of the surgical mesh connected with the other one of the insertion aids is disposed at a second location within the tissue, and engaging the actuator for moving the cutting element from a first position to a second position for severing the other one of the insertion aids from the connection with the other end of the surgical mesh.

In one embodiment, the method may include before severing the insertion aid form the mesh, pushing the one of the insertion aids into the tissue and pulling the one of the insertion aids out of the tissue for adjusting the position of the insertion aid.

In one embodiment, the system includes a first-hand insertion device, such as a left-hand insertion device, for securing the first insertion aid and a second-hand insertion device, such as a right-hand insertion device, for securing the second insertion aid.

In one embodiment, the implant insertion system is used for treating stress urinary incontinence (SUI), whereby the implant is used in women as a sub-urethral sling for the treatment of stress urinary incontinence resulting from urethral hypermobility and/or intrinsic sphincter deficiency.

In one embodiment, the implant is a surgical mesh having an overall length of about 6-16 cm, and more preferably about 12 cm. In one embodiment, the surgical mesh has a central zone that is about 3 cm long×1.1 cm wide, and first and second arms having lengths of about 4.5 cm and widths of about 0.95 cm. The arms are integrally attached to both ends of the central zone.

In one embodiment, the implant preferably includes a placement loop secured to the central region of the implant. In one embodiment, the placement loop is a sterile, single-patient use device consisting of a monofilament loop of PROLENE™ suture with an attached polypropylene button. The loop and the button are pre-assembled as part of the implant at the center of the mesh to aid in the placement of the central zone of the mesh under the urethra.

In one embodiment, when used with a surgical mesh, a function of the insertion aid is to aid in the insertion and positioning of the surgical mesh in a controlled manner. In one embodiment, the insertion aid preferably provides a tapered point connected to the end of a surgical mesh to aid with inserting the mesh into tissue. The tapered insertion aid desirably facilitates controlled implantation of the mesh by creating a tissue pathway without requiring the use of a scissor, blunt dissection, or knife dissection. The insertion aid can be pushed in or pulled out of the tissue, without being disconnected from the insertion device, for providing a surgeon with the ability to precisely position the mesh without causing unwanted tissue trauma. The insertion aid preferably holds the surgical mesh in a desired location until the insertion aid is intentionally separated from the connection with an end of the implant.

In one embodiment, the insertion aid has a diameter that is slightly smaller than the diameter of the distal end of the shaft of the insertion device. In one embodiment, the insertion aid has a diameter of about 3 mm, and the distal end of the shaft of the insertion device has a diameter of about 4 mm.

In one embodiment, the insertion aid has a conical or semi-conical distal geometry and a barb-less structure. This design preferably enables the insertion aid, prior to being severed and released from the connection with the implant, to be moved in proximal and distal directions within tissue for positioning the insertion tip in the tissue with minimal tissue trauma.

In one embodiment, the implant insertion system preferably includes two insertion devices, each having curved, stainless steel shafts with plastic handles incorporating actuators that are designed to deliver the implant. The inserters are provided as left-hand and right-hand insertion devices for engaging the two insertion aids attached to opposite ends of the implant.

In one embodiment, the distal end of the insertion device is designed to mate with the insertion aid such that the insertion aid can only be mounted to the insertion device in a single orientation. This design allows for the tip of the insertion aid to cooperate with the elongated shaft to resist bending that to date has only been achieved when using insertion tips made of metal.

In one embodiment, a return spring is connected with the actuator for returning the actuator to an initial start position after the actuator has been pushed distally. The return spring enables multiple firing of the insertion device in the event of reloading or test firing prior to final use.

In one embodiment, the implant insertion system includes an atraumatic winged guide, which is a stainless steel accessory instrument that facilitates consistent passage of the implant through the dissection tract. The winged guide is marked with an insertion zone to aid the surgeon's assessment of the inserted depth. The insertion zone indicates a distance of 3-4 cm from the tip of the winged guide.

These and other preferred embodiments of the present invention will be described in more detail below.

BRIEF DESCRIPTION OF THE DRAWING

FIG. 1A shows a surgical mesh having insertion aids connected with the respective first and second ends thereof, in accordance with one embodiment of the present invention.

FIG. 1B shows the surgical mesh of FIG. 1A including a first insertion aid connected with the first end of the surgical mesh, in accordance with one embodiment of the present invention.

FIG. 5A shows a magnified view of the distal end of the insertion device shown in FIG. 2, including an elongated shaft, an actuating wire, and a cutting element, in accordance with one embodiment of the present invention.

FIG. 5B shows the cutting element of FIG. 5A assembled with a distal end of the actuating wire of FIG. 5A, in accordance with one embodiment of the present invention.

FIG. 6A shows a distal end of an elongated shaft of an insertion device with a cutting element in a first position, in accordance with one embodiment of the present invention.

FIG. 6B shows a cross-sectional view of the elongated shaft and the cutting element of FIG. 6A taken along line 6B-6B thereof.

FIG. 7A shows the distal end of the elongated shaft of the insertion device of FIG. 6A with the cutting element in a second position that is proximal to the first position, in accordance with one embodiment of the present invention.

FIG. 7B shows a cross-sectional view of the elongated shaft and the cutting element of FIG. 7A taken along line 7B-7B thereof.

FIG. 8A shows the distal end of an elongated shaft of an insertion device with the cutting element in a first, extended position, in accordance with one embodiment of the present invention.

FIG. 9A shows the distal end of the elongated shaft of the insertion device of FIGS. 8A-8C with the cutting element in the second, retracted position.

FIG. 9C shows the distal end of the elongated shaft of the insertion device of FIGS. 9A and 9B with the cutting element moved back into the first, extended position.

FIG. 11A shows a cross-sectional view of a distal end of an elongated shaft of an insertion device with a cutting element in a first, extended position, in accordance with one embodiment of the present invention.

FIG. 11B shows the distal end of the insertion device of FIG. 11A with the cutting element moved into a second, retracted position that is proximal to the first position, in accordance with one embodiment of the present invention.

FIG. 13C shows a magnified view of the insertion aid of FIG. 13A secured to the end of the surgical mesh.

FIG. 13D shows a cross-sectional view of the insertion aid of FIGS. 13A-13C after the insertion aid has been inserted into an opening at the distal end of the elongated shaft of the insertion device, in accordance with one embodiment of the present invention FIG. 14 shows an implant including an insertion aid secured to the end of the implant, in accordance with another embodiment of the present invention.

FIG. 15 shows an implant including an insertion aid secured to the end of the implant, in accordance with yet another embodiment of the present invention.

DETAILED DESCRIPTION

Figure 2:
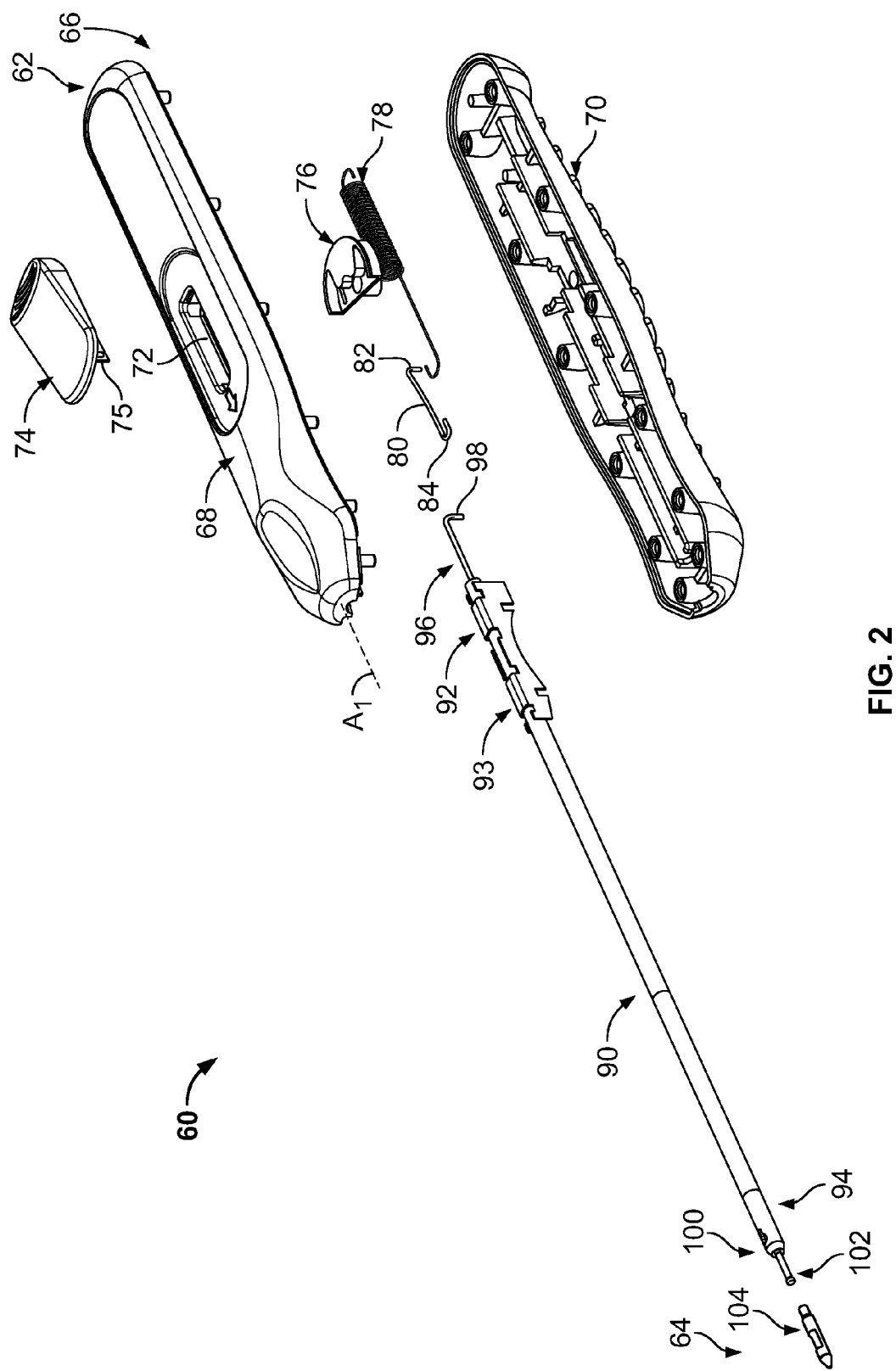
FIG. 2 shows an exploded view of an insertion device for implanting the surgical mesh shown in FIGS. 1A and 1B, in accordance with one embodiment of the present invention.

Referring to FIG. 1A, in one embodiment, a medical implant 30, such as a surgical mesh, preferably has a length $L_1$ of about 8-20 cm, and more preferably about 12 cm. The surgical mesh 30 has a central region 32 having a length $L_2$ of about 2.4 cm and more preferably about 3 cm, and a width $W_1$ of about 0.8-1.5 cm and more preferably about 1.1 cm. The implant 30 desirably includes first and second arms 34, 36 that are integrally formed with and extend from opposite ends of the central region 32. The first and second arms 34, 36 desirably have a length $L_3$ of about 3-5 cm and more preferably about 4.5 cm, and a width $W_2$ of about 0.5-1.2 cm and more preferably about 0.95 cm. Referring to FIGS. 1A and 1B, the implant 30 desirably has a first insertion aid 38 connected to the first end 40 of the first arm 34 via a first filament 42. Referring to FIG. 1A, the surgical mesh implant 30 preferably includes a second insertion aid 44 connected with an outer end 46 of the second arm 36 by a second filament 48. The first and second filaments 42, 48 that connect the respective first and second insertion aids 38, 44 with the outer ends of the first and second arms 34, 36 are preferably severable for separating the first and second insertion aids 38, 44 from their respective connections with the surgical mesh 30. As will be described in more detail herein, the first and second insertion aids 38, 44 are preferably used for coupling the ends of the surgical mesh 30 with one or more surgical tools, such as an insertion device, for advancing the implant 30 through tissue for implanting the surgical mesh implant 30 at a desired location within the tissue.

In one embodiment, the insertion aids may be attached directly to the ends of the arms of the implant, without requiring the use of filaments. In one embodiment, the arms may be rolled into a circular shape that has the appearance of an elongated element such as a filament and the outer ends of the rolled arms may be connected with insertion aids.

In one embodiment, the mesh material is preferably made of polypropylene, or a combination of polypropylene and MONOCRYL absorbable material. In one embodiment, the implant preferably includes a mesh, such as a shaped piece of blue (phthalocyanine blue, color index number 74160) PROLENE™ polypropylene mesh. The implant is attached to two insertion aids such as violet (D&C violet no. 2, color index number 60725) PDS™ (Polydioxanone) absorbable insertion aids. The absorbable insertion aids are preferably molded from polydioxanone identical in composition to that used in PDS™ II (polydioxanone) suture.

In one embodiment, the first and second insertion aids 38, 44 have an outer diameter $OD_1$ of about 2-5 mm, and more preferably about 2 mm. The first and second insertion aids preferably have a diameter that is less than or equal to the width $W_2$ of the first and second arms. The first and second insertion aids 38, 44 may have a wide variety of geometric shapes including spheres, circles, squares, rectangles, tubes, cubes, parallelograms, etc.

In one embodiment, the surgical mesh implant 30 is a sterile device that is intended to be used one time on a single patient. In one embodiment, the surgical mesh implant 30 preferably includes an adjusting element 50 having a loop 52 secured to the central region 32 of the surgical mesh implant 30 and a graspable button 54 attached to the loop 52. In one embodiment, the loop 52 is a monofilament loop preferably made of prolene, such as a prolene suture, and the graspable button 54 is made of polypropolene. The loop 52 and the button 54 connected with the central region 32 of the surgical mesh implant 30 desirably aid in the placement and alignment of the central region 32 of the surgical mesh under a body part such as a urethra.

Referring to FIG. 2, in one embodiment, an insertion device 60 is utilized for implanting the surgical mesh 30 shown in FIGS. 1A and 1B. The insertion device 60 desirably includes a proximal end 62 and a distal end 64 remote therefrom. The proximal end 62 of the insertion device 60 includes a handle 66 having a top half 68 and a bottom half 70 that are assembled together. The top half 68 of the handle includes an elongated actuator slot 72 that extends along a longitudinal axis $A_1$ of the insertion device 60. An actuator 74 is adapted to slide within the elongated actuator slot 72 for enabling the actuator 74 to slide in distal and proximal directions along the longitudinal axis $A_1$ of the insertion device 60.

Figure 3:
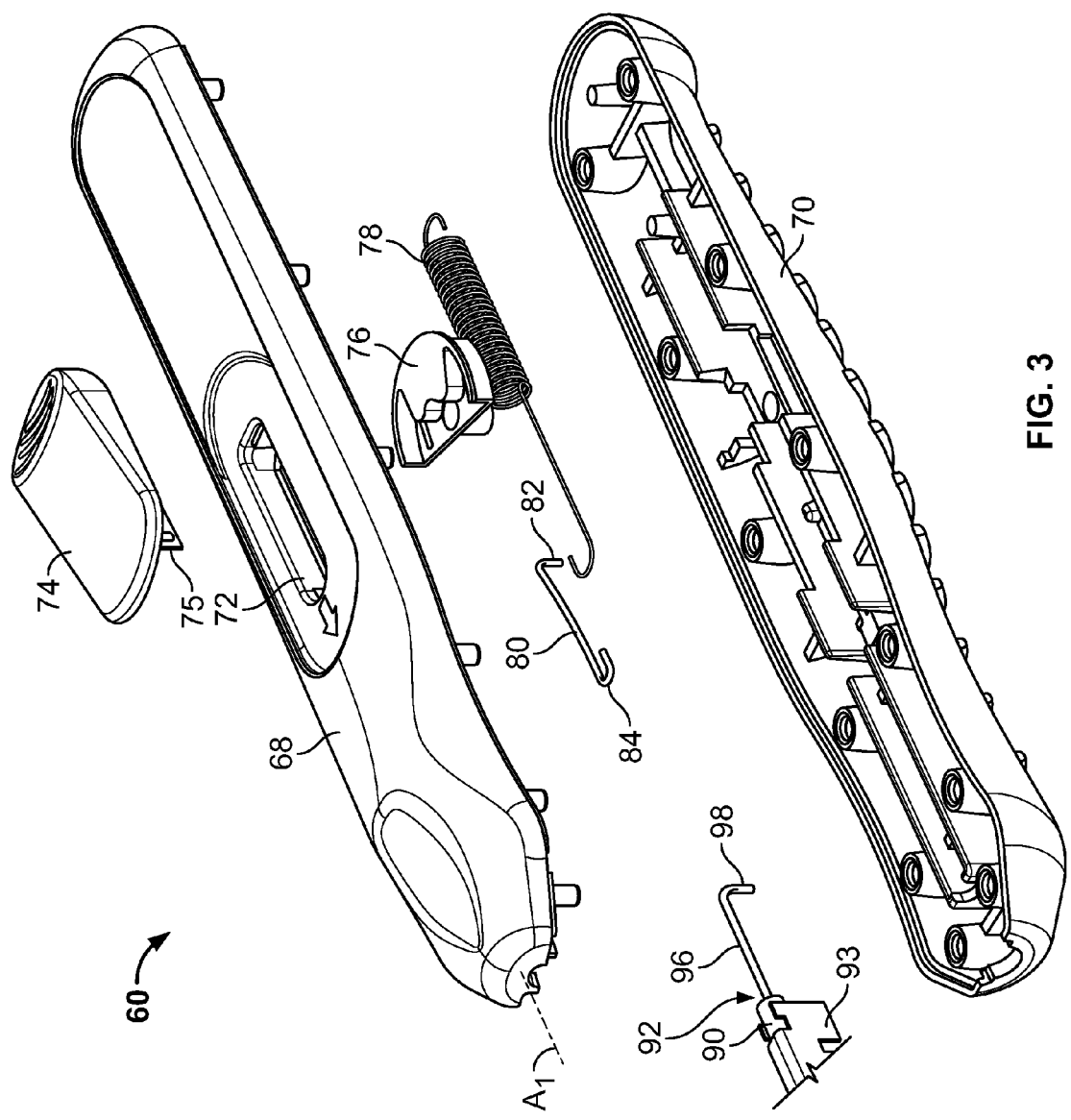
FIG. 3 shows an exploded view of a handle of the insertion device shown in FIG. 2, in accordance with one embodiment of the present invention.

Referring to FIGS. 2 and 3, in one embodiment, the insertion device 60 includes a rotatable cam element 76 that is mounted on the bottom half 70 of the handle 66. The cam element 76 is adapted to rotate in clockwise and counter-clockwise directions after being mounted onto the bottom half 70 of the handle as will be described in more detail herein. The insertion device 60 includes an actuator release spring 78 that stores energy therein as the actuator 74 is moved distally along axis $A_1$. The release spring 78 is designed to store energy as the actuator 74 is pushed distally, and then, when the actuator 74 is released, use the stored energy to return the actuator 74 toward the proximal end 62 of the insertion device 60. The insertion device 60 preferably includes a pull wire 80 having a proximal end 82 connected with the rotatable cam element 76 and a distal end 84 connected with an underside 75 of the actuator 74.

Figure 4:
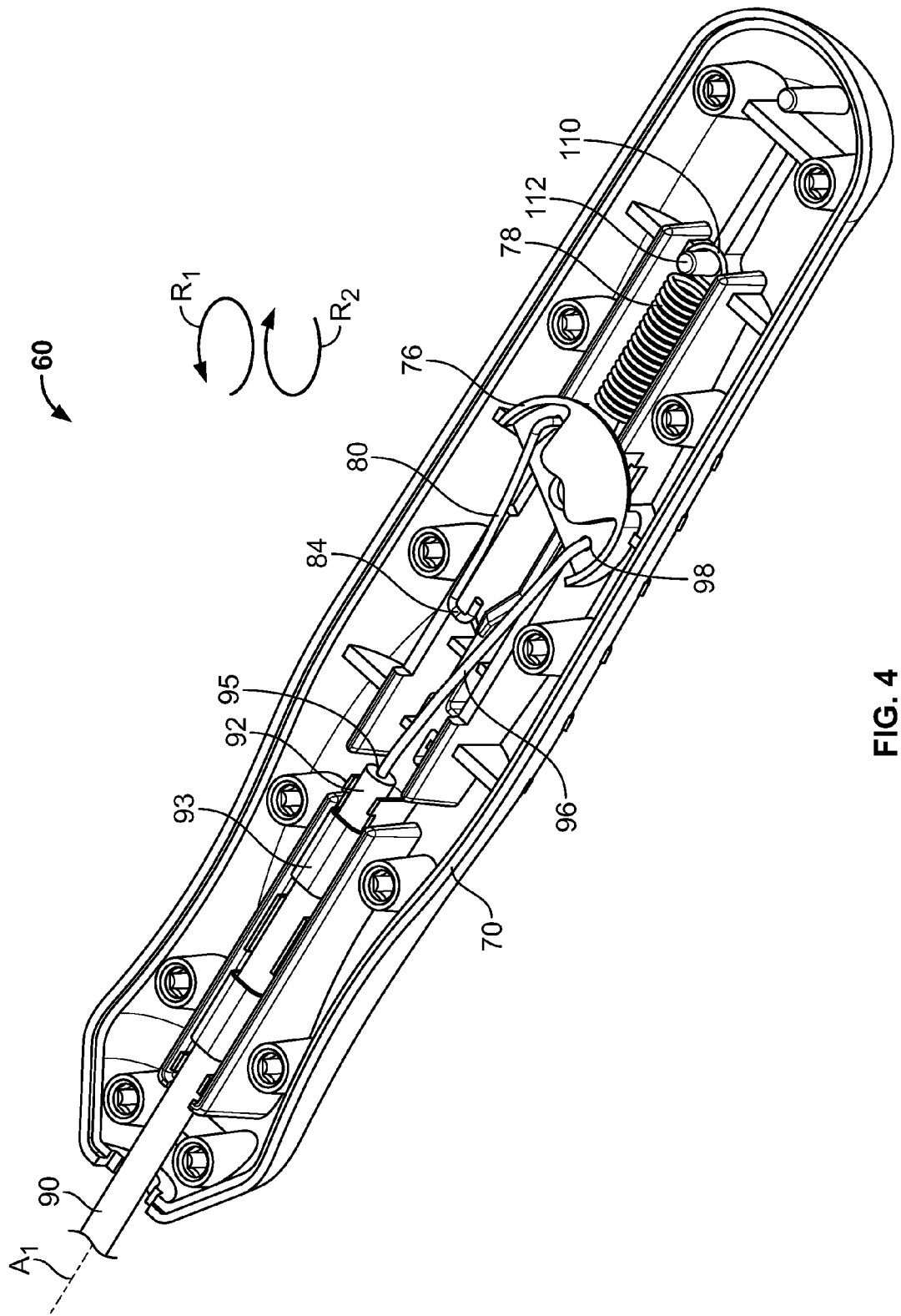
FIG. 4 shows the handle of the insertion device shown in FIG. 2 with the top half of the handle removed, in accordance with one embodiment of the present invention.

Referring to FIGS. 2-4, the insertion device 60 desirably includes an elongated shaft 90 having a proximal end 92 connected to a distal end of the bottom half 70 of the handle 66 via a weldment 93 and a distal end 94 remote therefrom. The elongated shaft 90 desirably has a tubular shape with a proximal opening 95 (FIG. 4) at the proximal end 92 of the shaft, a distal opening at the distal end 94 of the shaft 90 and an elongated conduit that extends between the proximal end 92 and the distal end 94. The insertion device 60 includes an actuating wire 96 that extends through the elongated conduit of the elongated shaft 90 and is adapted to slide in distal and proximal directions relative to the elongated shaft 90. The actuating wire 96 includes a proximal end 98 that is connected with the rotatable cam element 76. Referring to FIG. 2, in one embodiment, the actuating wire 96 preferably includes a distal end 100 with an enlarged head 102 that is received within an opening at the proximal end of a cutting element 104 for assembling the cutting element 104 with the distal end 100 of the actuating wire 96.

Referring to FIGS. 3 and 4, in one embodiment, the proximal end 92 of the elongated shaft 90 is assembled with the bottom half 70 of the handle 66 so that the elongated shaft 90 extends along the longitudinal axis $A_1$ of the insertion device 60. The rotatable cam element 76 is mounted on the bottom half 70 of the handle 66 so that the cam element 76 is able to rotate in a first counter-clockwise direction designated $R_1$, and a second clockwise direction designated $R_2$ (FIG. 4). The return spring 78 is disposed within a molded part of the bottom half 70 of the handle 66 with a proximal end 110 secured to a projection 112 of the bottom half 70 of the handle 66 and a distal end (not shown) connected with an underside of the rotatable cam element 76.

Referring to FIGS. 3 and 4, in one embodiment, the insertion device 60 includes the pull wire 80 having the proximal end 82 connected with the rotatable cam element 76 and the distal end 84 connectable with the underside 75 of the actuator 74. The proximal end 98 of the actuating wire 96 is connected with an opposite side of the rotatable cam element 76, and the actuating wire 96 extends through the elongated conduit of the elongated shaft 90 for engaging the cutting element 104 (FIG. 2) at the distal end 94 of the shaft 90.

Referring to FIGS. 2-4, in one embodiment, as the actuator 74 is pushed distally along the axis $A_1$ the underside 75 of the actuator 74 pulls the distal end 84 of the pull wire 80 toward the distal end 64 of the insertion device 60. As the pull wire 80 moves distally, the proximal end 82 of the pull wire 80 that is connected with the rotatable cam element 76 rotates the cam element 76 in the counter-clockwise direction $R_1$. As the cam element 76 rotates in the counter-clockwise direction $R_1$, the cam element 76 pulls the proximal end 98 of the actuating wire 96 toward the proximal end 66 of the insertion device 60 for retracting the actuating wire 96 relative to the elongated shaft 90. As the rotatable cam element 76 is rotated in the counter-clockwise direction $R_1$, the return spring 78, which is connected with the rotatable cam 76, is stretched for storing potential energy in the return spring. When the actuator 74 is released, the energy stored in the return spring 78 urges the rotatable cam element 76 to rotate in the clockwise direction $R_2$. As the cam element 76 rotates in the clockwise direction $R_2$, the cam element 76 urges the proximal end 98 of the actuating wire 96 to move distally for advancing the actuating wire 96 in a distal direction relative to the elongated shaft 90 which moves the cutting element 104 distally. As the actuating wire 96 moves proximally and distally relative to the elongated shaft 90, the cutting element 104 moves simultaneously with the actuating wire 96.

Referring to FIG. 5A, in one embodiment, the cutting element 104 is adapted to be connected with the distal end 100 of the actuating wire 96. The cutting element 104 preferably includes a proximal end 120 having a proximal end opening adapted to receive and seat the enlarged head 102 at the distal end 100 of the actuating wire 96. The cutting element 104 includes a distal end 122 having a pointed tip 124, and a tubular body 126 that extends proximally from the pointed tip 124. The cutting element 104 has an elongated lateral opening 128 formed in an outer wall of the tubular body 126. The elongated lateral opening 128 has a pair of side walls 130A, 130B that extend along the longitudinal axis $A_1$, a proximal end wall 132 that traverses the longitudinal axis $A_1$ and a distal end wall 134 with a cutting edge that also traverses the longitudinal axis $A_1$.

In one embodiment, the actuating wire 96 moves freely in proximal and distal directions within the elongated conduit of the elongated shaft 90. In one embodiment, the cutting element 104 is located adjacent the distal end 94 of an outer shaft.

In one embodiment, the outer shaft has a curved section that is proximal to the distal end of the outer shaft. In one embodiment, the distal-most end of the outer shaft (i.e. a section that is distal to the curved section) is straight.

In one embodiment, the distal end 94 of the elongated shaft 90 has an opening 140 with a keyhole shape, including a wider distal section 142 adjacent the distal end of the keyhole shaped opening 140 and a narrower proximal section 144 adjacent the proximal end of the keyhole shaped opening 140.

Referring to FIGS. 5A and 5B, in one embodiment, the cutting element 104 is assembled with the distal end 100 of the actuating wire 96 so that the tubular body 126 of the cutting element 104 extends along the longitudinal axis $A_1$. After the cutting element 104 is assembled with the actuating wire 96, the cutting element 104 and the actuating wire 96 are adapted to travel together simultaneously in proximal and distal directions along the longitudinal axis $A_1$ of the insertion device 60. As the cutting element 104 and the actuating wire 96 slide together along the longitudinal axis $A_1$, they move relative to the elongated shaft 90 of the insertion device 60 and the keyhole shaped opening 140 formed in the shaft 90.

In one embodiment, the insertion device 60 disclosed herein is adapted to move the cutting element 104 between a first position in which the tip 124 of the cutting element extends beyond the distal end 94 of the elongated shaft 90 and a second position in which the tip 124 is retracted inside the elongated shaft 90. FIGS. 6A and 6B show the cutting element 104 in the extended, first position relative to the distal end 94 of the elongated shaft 90. In the first position, the distal tip 124 of the cutting element 104 extends beyond the tapered distal end 94 of the elongated shaft 90, and the lateral opening 128 formed in the tubular body 126 of the cutting element 104 is aligned with the keyhole opening 140 formed in the elongated shaft 90. FIG. 6B shows the enlarged head 102 at the distal end 100 of the actuating wire 96 seated against an inner surface of the tubular body 126 of the cutting element 104 for forming a connection between the proximal end 120 of the cutting element 104 and the distal end 100 of the actuating wire 96. As a result of the connection between the actuating wire 96 and the cutting element 104, the two components move together simultaneously along the axis $A_1$.

Referring to FIGS. 7A and 7B, in one embodiment, when the actuator 74 shown in FIGS. 2-4 is pushed along the axis $A_1$ toward the distal end of the insertion device, the rotatable cam 76 in the bottom half 70 of the handle (FIG. 4) rotates in the counter-clockwise direction $R_1$ for retracting the actuating wire 96 toward the proximal end 62 of the insertion device 60. As the actuating wire 96 moves proximally in the direction designated DIR1, the actuating wire 96 pulls the cutting element 104 connected therewith in the proximal direction DIR1. As the cutting element 104 is pulled in the proximal direction, the cutting edge 134 moves proximally relative to the keyhole opening 140 until the cutting edge 134 of the cutting element 104 is proximal to the proximal end of the narrower section 144 of the keyhole opening 140. When the cutting element 104 has been retracted to the second position shown in FIGS. 7A and 7B, the tip 124 is retracted into the elongated shaft 90 so that the tip 124 of the cutting element is proximal to the distal end 94 of the elongated shaft 90.

Figure 8B:
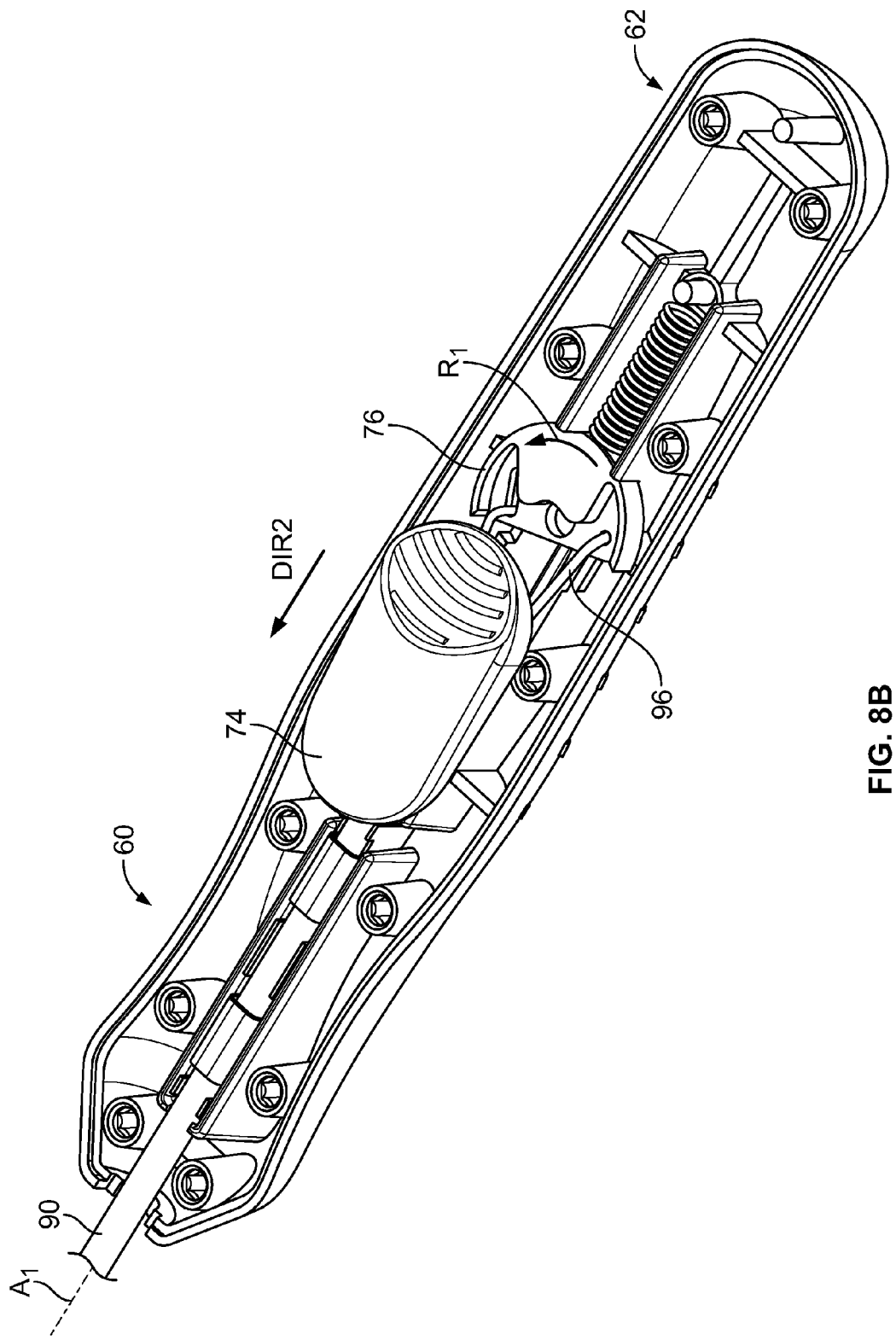
FIG. 8B shows a handle end of the insertion device of FIG. 8A with an actuator advanced distally for moving the cutting element shown in FIG. 8A.
Figure 8C:
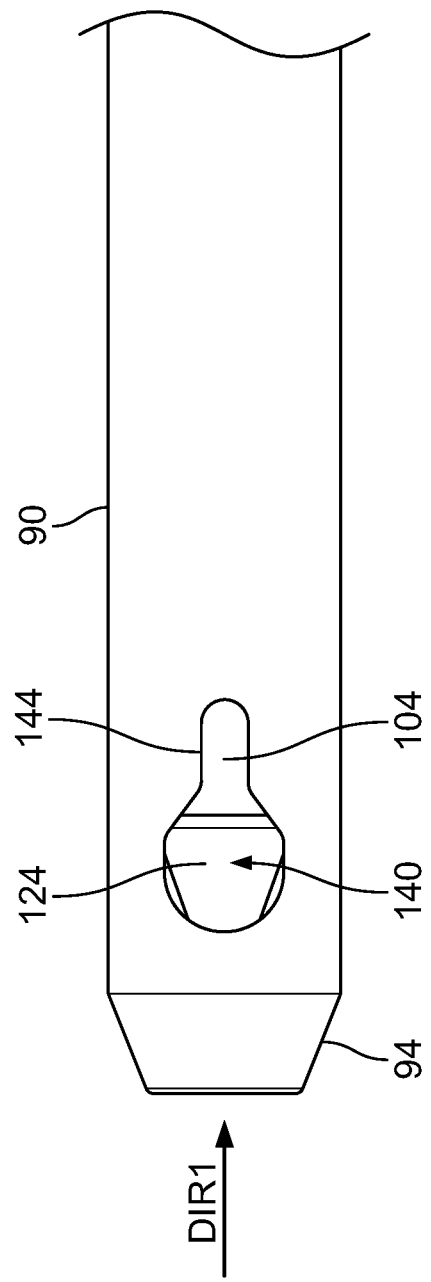
FIG. 8C shows the cutting element of FIG. 8A after being moved from the first, extended position of FIG. 8A to a second, retracted position.

Referring to FIGS. 8A-8C, in one embodiment, the cutting element 104 is moved from an extended, first position (FIG. 8A) to a retracted, second position (FIG. 8C). Referring to FIG. 8A, in one embodiment, the insertion device is in the first position so that the tip 124 of the cutting element 104 extends beyond the distal end 94 of the elongated shaft 90. The lateral opening 128 formed in the tubular body of the cutting element 104 is aligned with the keyhole opening 140 formed in the elongated shaft 90.

Referring to FIG. 8B, the actuator 74 is advanced in a distal direction DIR2 along the axis $A_1$ toward the distal end of the elongated shaft 90. As the actuator 74 moves distally, the rotatable cam element 76 is rotated in the counter-clockwise direction $R_1$ for pulling the actuating wire 96 toward the proximal end 62 of the insertion device 60.

Referring to FIGS. 8B and 8C, as the actuating wire 96 moves proximally, the distal end of the actuating wire 96 retracts in the direction DIR1 to move the cutting element 104 from the first position (FIG. 8A) to the second position shown in FIG. 8C. In the second position, the tip 124 of the cutting element 104 is retracted within the elongated shaft 90 so that the tip 124 is proximal to the distal end 94 of the elongated shaft 90. Moreover, the cutting edge 134 of the cutting element 104 is proximal to the narrower section 144 of the keyhole opening 140, as shown in FIG. 7B.

Figure 9B:
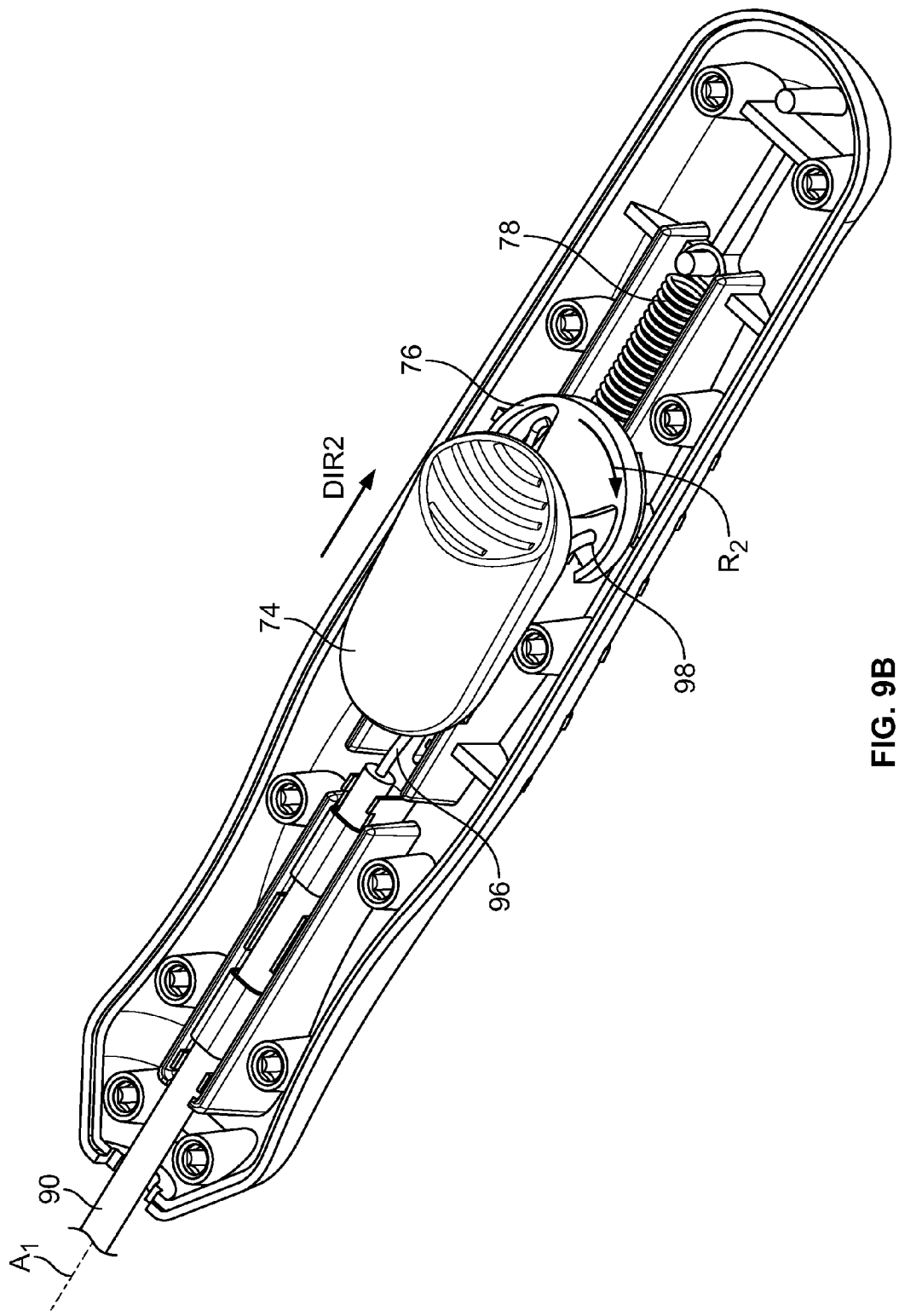
FIG. 9B shows the handle end of the insertion device of FIG. 9A with the actuator returning toward the proximal end of the insertion device for moving the cutting element back to the first, extended position.

Referring to FIGS. 9A-9C, in one embodiment, when the actuator 74 is released, the actuator 74 is urged to slide proximally along the axis $A_1$ by the return spring 78 for enabling the cutting element to move back into the extended, first position. Referring to FIG. 9A, with the actuating element 74 pushed distally (FIG. 8B), the cutting element 104 is retracted in the second position relative to the outer shaft 90. Referring to 9B, with the cutting element in the retracted position, the actuator 74 may be released so that it moves proximally (DIR2) under the force of the return spring 78 toward the proximal end of the insertion device. The return spring 78 rotates the cam element 76 in the clockwise direction $R_2$. As the cam element 76 rotates in the clockwise direction $R_2$, the cam element 76 urges the distal end 98 of the actuating wire 96 to move distally within the elongated conduit of the elongated shaft 90, which, in turn, moves the cutting element 104 in the direction DIR1 and back to the extended, first position shown in FIG. 9C. When the cutting element 104 is in the extended, first position shown in FIG. 9C, the tip 124 extends beyond the distal end 94 of the elongated shaft 90 and the lateral opening 128 formed in the cutting element is once more aligned with the keyhole opening in the elongated shaft.

Figure 10A:
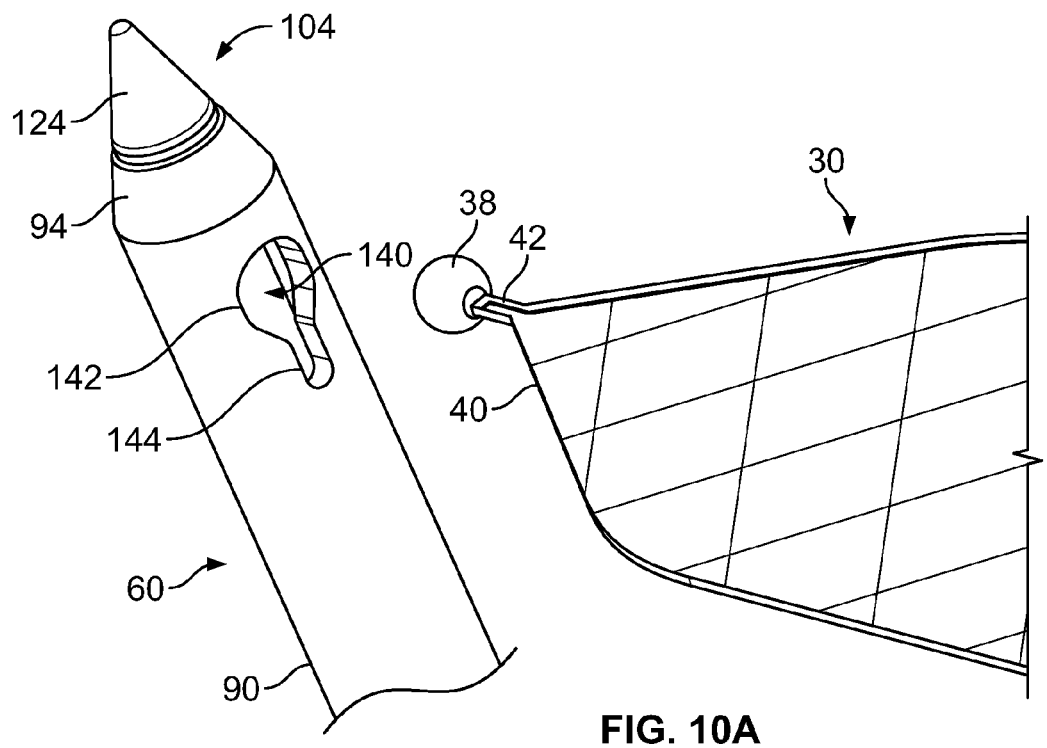
FIGS. 10A-10E show a method of connecting a surgical mesh having an insertion aid with an insertion device and moving a cutting element at a distal end of the insertion device from a first position to a second position for severing the insertion aid from an end of the surgical mesh, in accordance with one embodiment of the present invention.

In one embodiment, the insertion device disclosed herein is utilized for implanting a surgical mesh in tissue. Referring to FIG. 10A, in one embodiment, the surgical mesh 30 includes a first insertion aid 38 that is connected to the first end 40 of the surgical mesh via a filament 42. The filament may include one or more strands of thread that connect the insertion aid to the implant. In one embodiment, the filament 42 may be severed for separating the insertion aid 38 from the surgical mesh 30.

In one embodiment, the insertion aid 38 is juxtaposed with the keyhole opening 140 formed in the elongated shaft 90. The cutting element 104 is preferably in the extended, first position so that the tip 124 extends beyond the distal end 94 of the outer shaft 90. The insertion aid 38 is able to pass through the wider distal section 142 of the keyhole opening 140 but not the narrower proximal section 144 of the keyhole opening.

Figure 10B:
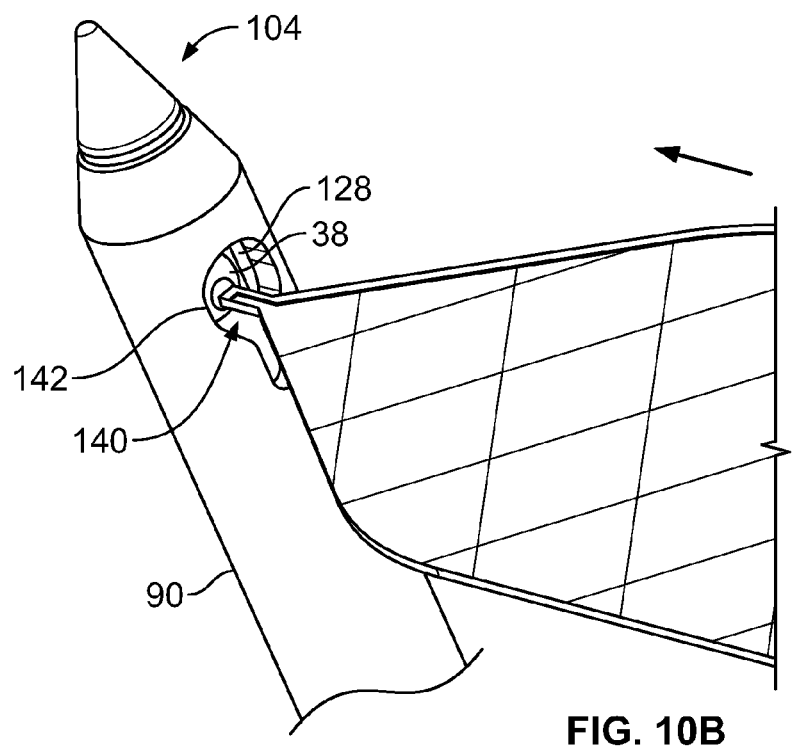

Referring to FIG. 10B, in one embodiment, the first insertion aid 38 is passed through the wider distal section 142 of the keyhole opening 140 formed in the elongated shaft 90 and the elongated lateral opening or window 128 formed in the tubular body of the cutting element 104.

Figure 10C:
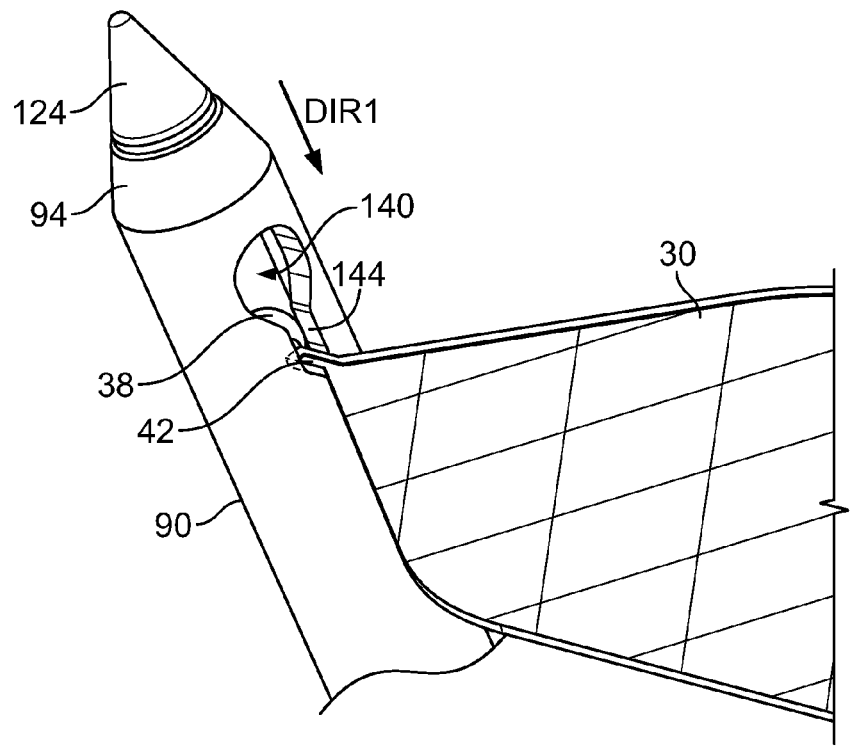

Referring to FIG. 10C, in one embodiment, the first insertion aid 38 is moved in a proximal direction DIR1 relative to the outer shaft 90 so that the filament 42 connecting the first insertion aid 38 with the surgical mesh 30 is disposed within the narrower section 144 of the keyhole opening 140. The first insertion aid 38 and the surgical mesh 30 are now secured to the elongated shaft 90 of the insertion device 60 because the larger diameter first insertion aid 38 cannot pass through the width of the narrower section 144 of the keyhole opening 140.

With the tip 124 of the cutting element 104 extended, as shown in FIG. 10C, the tip 124 may be utilized for advancing the distal end 94 of the elongated shaft 90 through tissue for implanting the surgical mesh 30 within the tissue. The sharpened or pointed tip 124 of the cutting element desirably facilitates advancement of the distal end 94 of the elongated shaft 90 through the tissue. As the elongated shaft 90 advances through the tissue, the surgical mesh 90 is pulled through the tissue by the insertion device.

Figure 10D:
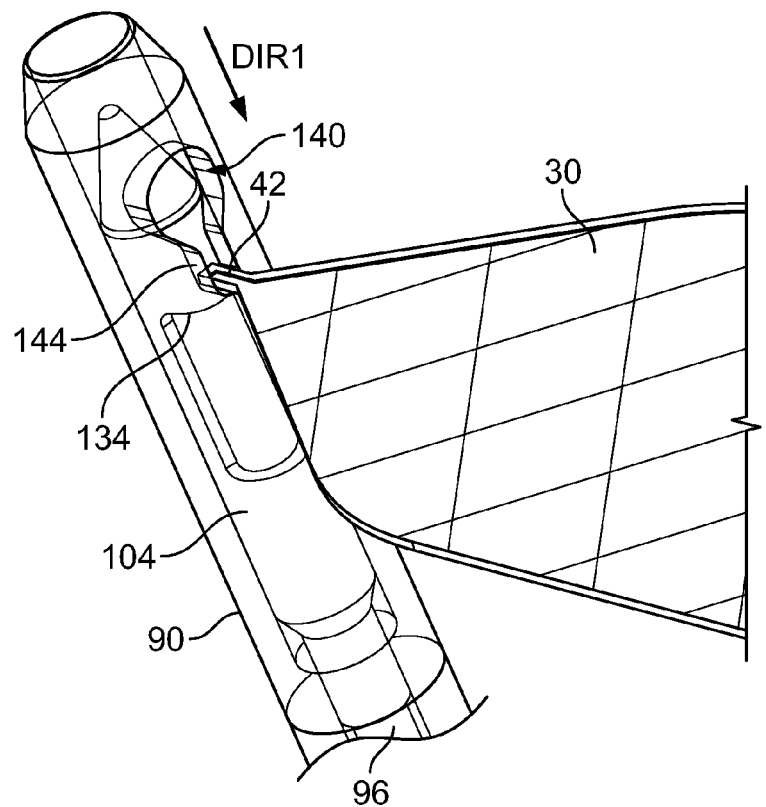

Referring to FIG. 10D, after the end of the surgical mesh 30 connected with the elongated shaft 90 has been advanced to a desired location in the tissue, it may be desirable to sever the filament 42 connecting the first insertion aid 38 (FIG. 10C) with the surgical mesh 30. In one embodiment, the actuator 75 (FIG. 8B) is pressed distally (DIR2), which, in turn, moves the actuating wire 96 and the cutting element 104 in a proximal direction DIR1. As the cutting element 104 moves proximally, the distal cutting edge 134 of the cutting element 104 moves proximal to the proximal end of the narrower section 144 of the keyhole opening 140. As the cutting edge 134 moves proximally relative to the narrower section 144, the filament 42 connecting the insertion aid 38 (FIG. 10A) with the surgical mesh 30 is severed by the cutting edge 134 of the cutting element 104.

Figure 10E:
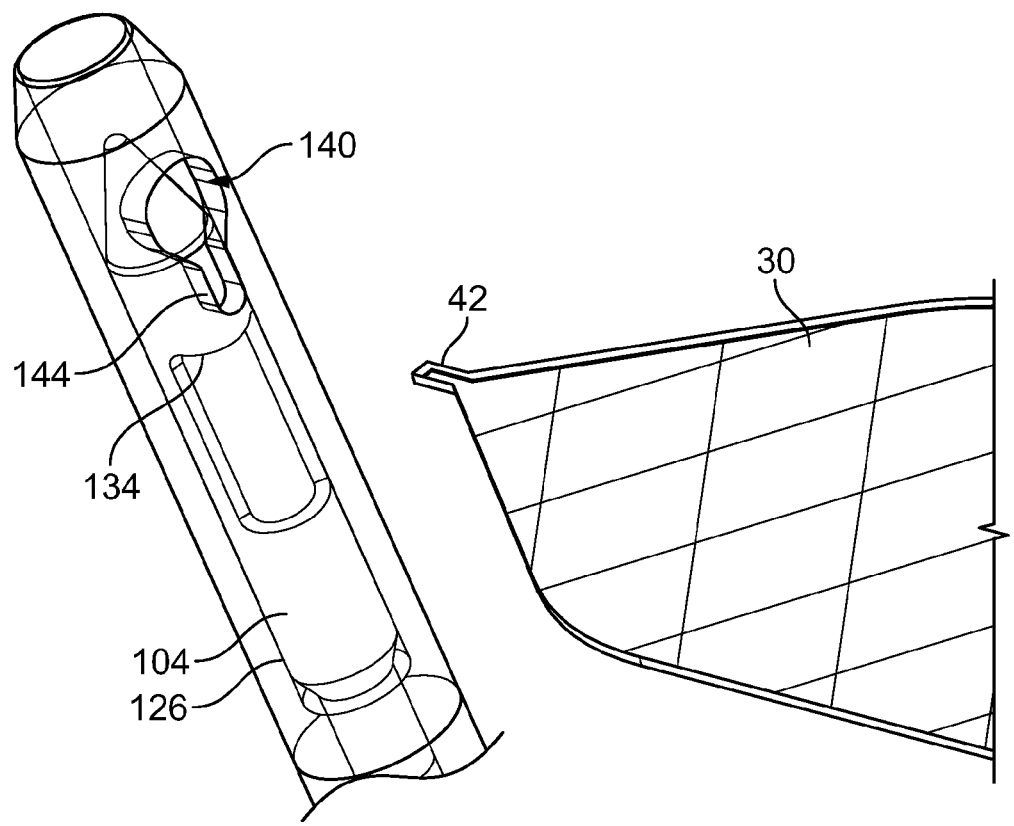

FIG. 10E shows the filament 42 after it has been severed by the cutting edge 134 of the cutting element 104. As shown in FIG. 10E, the cutting edge 134 is proximal to the proximal end of the narrower section 144 of the keyhole opening 140. After the first insertion aid has been severed from its attachment with the surgical mesh 30, the first insertion aid preferably remains inside the tubular body 126 of the cutting element 104 for being removed from the tissue when the elongated shaft is withdrawn from the surgical opening.

In one embodiment, the pointed tip is not provided on the cutting element but is instead provided at the distal end of the shaft. Referring to FIGS. 11A and 11B, in one embodiment, an insertion device for implanting a surgical mesh having one or more insertion aids preferably includes an elongated shaft 290 having a distal end 294 with a pointed tip 324. The elongated shaft 290 has a keyhole opening 340 formed in an outer wall thereof including a wider section 342 and a narrower section 344 that is proximal to the wider section 342.

The insertion device preferably includes an actuating wire 296 having an enlarged head 302 at a distal end 300 of the actuating wire. The actuating wire 296 is adapted to be telescopically received within the elongated shaft 290, and to move in proximal and distal directions relative to the elongated shaft 290 along a longitudinal axis of the insertion device designated $A_1$.

The insertion device also desirably includes a cutting element 304 having a tubular-shaped body 326 with an elongated opening 328 formed in an outer wall of the tubular body 326. The elongated opening 328 includes opposing side walls that extend along the longitudinal axis $A_1$, a proximal wall 332 that traverses the longitudinal axis $A_1$, and a distal wall 334 having a cutting edge that also traverses the longitudinal axis $A_1$. The tubular body 326 desirably has an axial opening at a proximal end 320 of the cutting element 304. The axial opening receives the enlarged head 302 at the distal end 300 of the actuating wire 296 for mounting the cutting element 304 onto the distal end 300 of the actuating wire 296. After the cutting element 304 has been assembled with the actuating wire 296, the cutting element 304 and the actuating wire 296 are adapted to move simultaneously with one another in proximal and distal directions and relative to the elongated shaft 290 and the keyhole opening 340, along the longitudinal axis $A_1$ of the insertion device.

In one embodiment, the cutting element 304 is moveable between a first, extended position and a second, retracted position. FIG. 11A shows the cutting element 304 in the first, extended position, whereby the elongated opening 328 of the cutting element 304 is aligned with the keyhole opening 340 formed in the outer shaft 290 of the insertion device. In the first position, the cutting edge 334 is in general alignment with the distal end of the wider section 342 of the keyhole opening 340.

Referring to FIG. 11B, when the actuator button on the handle is pushed in a distal direction toward the tip 324 of the elongated shaft 290, the actuating wire 296 and the cutting element 304 move together in a proximal direction toward the proximal end of the insertion device until the cutting element 304 reaches the second, retracted position shown in FIG. 11B. In this position, the elongated opening 328 formed in the tubular body 326 of the cutting element 304 is proximal to the keyhole opening 340 formed in the elongated shaft 290. In addition, the cutting edge 334 of the elongated lateral opening 328 is proximal to the proximal end of the narrower section 344 of the keyhole opening 340. As will be described in more detail herein, as the cutting edge 334 of the cutting element 304 moves from the first, extended position shown in FIG. 11A to the second, retracted position shown in FIG. 11B, the cutting edge 334 passes closely by the inner surface of the outer shaft 290 located at the proximal end of the narrower section 344 of the keyhole opening 340 to sever a filament connecting an insertion aid with an end of a surgical implant, such as a surgical mesh implant.

Figure 12A:
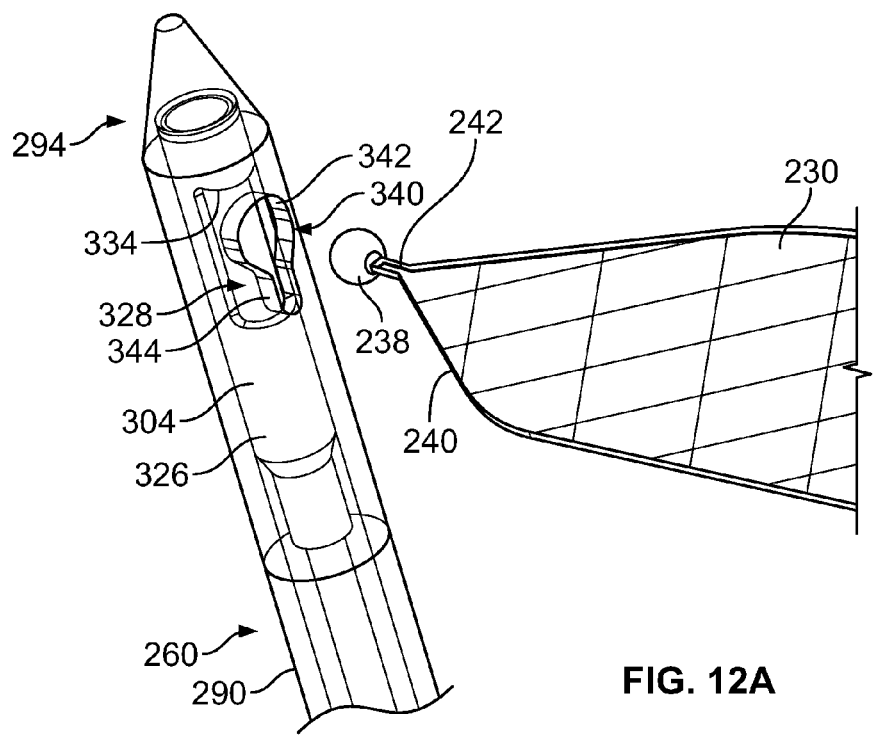
FIGS. 12A-12E show a method of connecting a surgical mesh having an insertion aid with an insertion device and moving a cutting element from a first position to a second position for severing the insertion aid from an end of the surgical mesh, in accordance with one embodiment of the present invention.

Referring to FIG. 12A, in one embodiment, a surgical mesh implant 230 preferably includes an insertion aid 238 that is connected to a first end 240 of the surgical mesh 230 by a filament 242. The filament 242 may include one or more strands of thread that connect the insertion aid 238 to the mesh implant 230. In one embodiment, the filament 242 may be severed for separating the insertion aid 238 from the surgical mesh 230. In order to connect the surgical mesh 230 with a distal end 294 of an elongated shaft 290 of an insertion device, the insertion aid 238 is juxtaposed with a keyhole opening 340 formed in the outer wall of the elongated shaft 290. The insertion aid 238 has a diameter that is smaller than the opening defined by the wider section 342 of the keyhole opening 340 and larger than the opening defined by the narrower section 344 of the keyhole opening 340.

In one embodiment, the insertion aids may be attached directly to the ends of the implant, without requiring the use of filaments. In one embodiment, one or more of the ends of an implant may be rolled into a circular shape that has the appearance of an elongated element, such as a filament, and the one or more rolled ends may be connected with insertion aids.

In FIG. 12A, the cutting element 304 is in the first, extended position (FIG. 11A) so that the elongated opening 328 formed in the tubular body 326 of the cutting element 304 is generally aligned with the keyhole opening 340 of the elongated shaft 290. Moreover, the cutting edge 334 at the distal end of the elongated lateral opening 328 is generally aligned with the distal end of the wider section 342 of the keyhole opening 340.

Figure 12B:
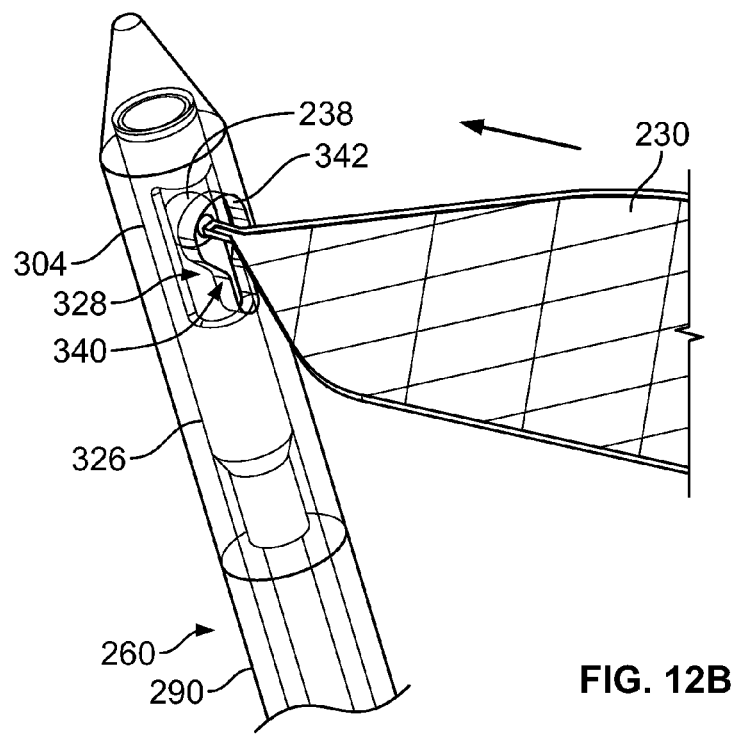

Referring to FIG. 12B, in one embodiment, in order to connect the surgical mesh 230 with the insertion device 260, the insertion aid 238 is passed through the wider section 342 of the keyhole opening 340 formed in the outer shaft 290, and then through the elongated opening 328 formed in the tubular body 326 of the cutting element 304, whereupon the insertion aid 238 is disposed within the tubular body 326 of the cutting element 304.

Figure 12C:
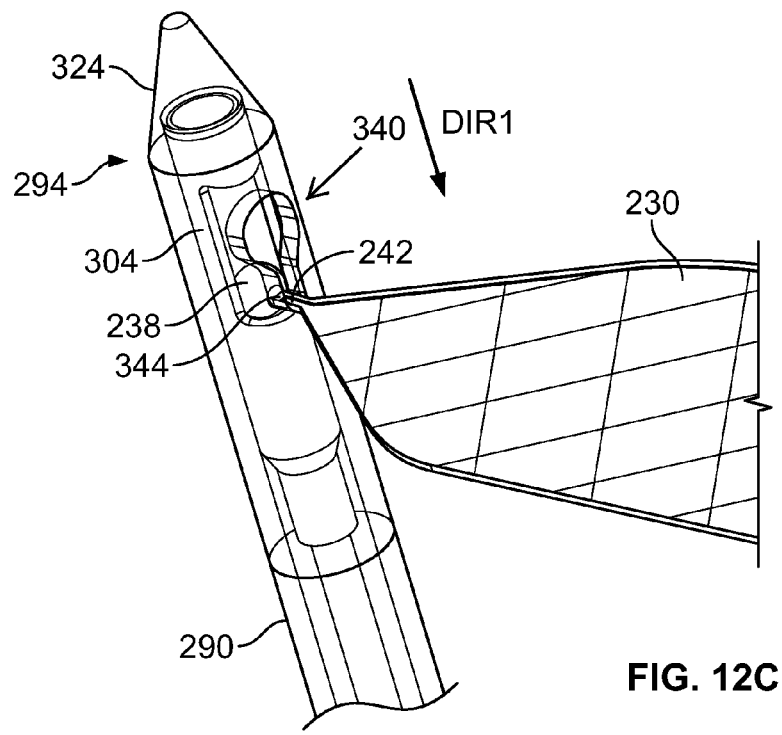

Referring to FIG. 12C, in one embodiment, the insertion aid 238 is shifted in the proximal direction DIR1 relative to the cutting element 304 and the keyhole opening 340 formed in the elongated shaft 290 so that the filament 242 connecting the insertion aid 238 with the surgical mesh 230 passes through the narrower section 344 of the keyhole opening 340. As noted above, because the insertion aid 238 has a larger diameter than the width of the narrower section 344 of the keyhole opening 340, the insertion aid 238 cannot pass through the narrower section 344 of the keyhole opening 340 when in the position shown in FIG. 12C. At this stage, the surgical mesh 230 is secured to the elongated shaft 290 of the insertion device. The tip 324 at the distal end 294 of the elongated shaft 290 may be utilized for advancing the shaft 290 and the surgical mesh 230 secured therewith through tissue for implanting the surgical mesh 230 in the tissue.

Figure 12D:
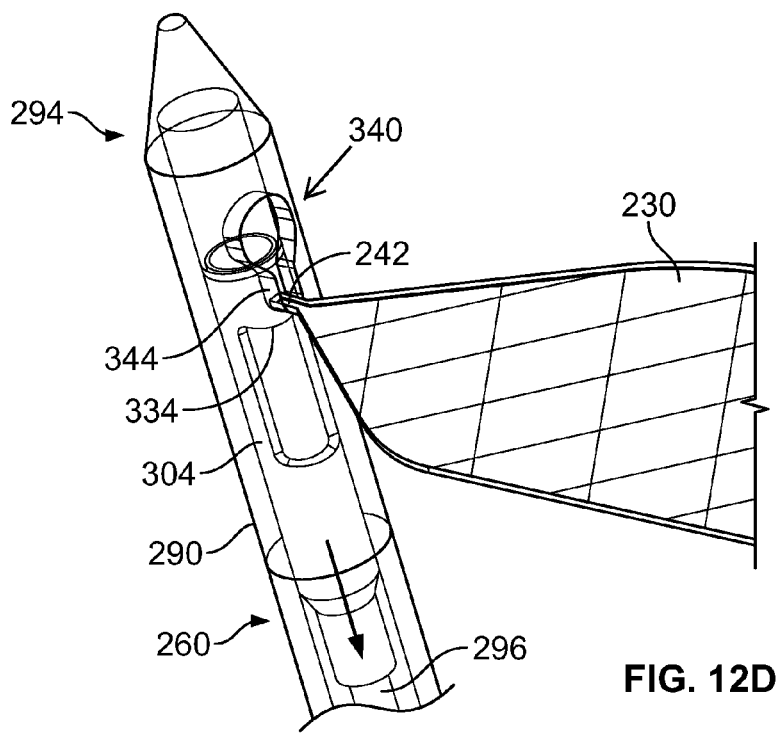

Once the insertion device 260 has been utilized to advance the surgical mesh 230 to a desired location within the tissue, the surgical mesh 230 may be detached from its connection with the elongated shaft 290 of the insertion device 260. Referring to FIG. 12D, in one embodiment, an actuator 74 (FIGS. 2-4) is pushed toward a distal end 294 of the insertion device 260, which, in turn, pulls the actuating wire 296 toward the proximal end of the insertion device 260. As the actuating wire 296 moves proximally, the cutting element 304 also moves simultaneously with the actuating wire 296 in the proximal direction. When the cutting element 304 reaches the second, retracted position shown in FIG. 12D, the distal cutting edge 334 of the cutting element 304 is proximal to the proximal end of the narrower section 344 of the keyhole opening 340 for severing the filament 242 connecting the insertion aid 238 (FIG. 12A) with the surgical mesh 230.

Figure 12E:
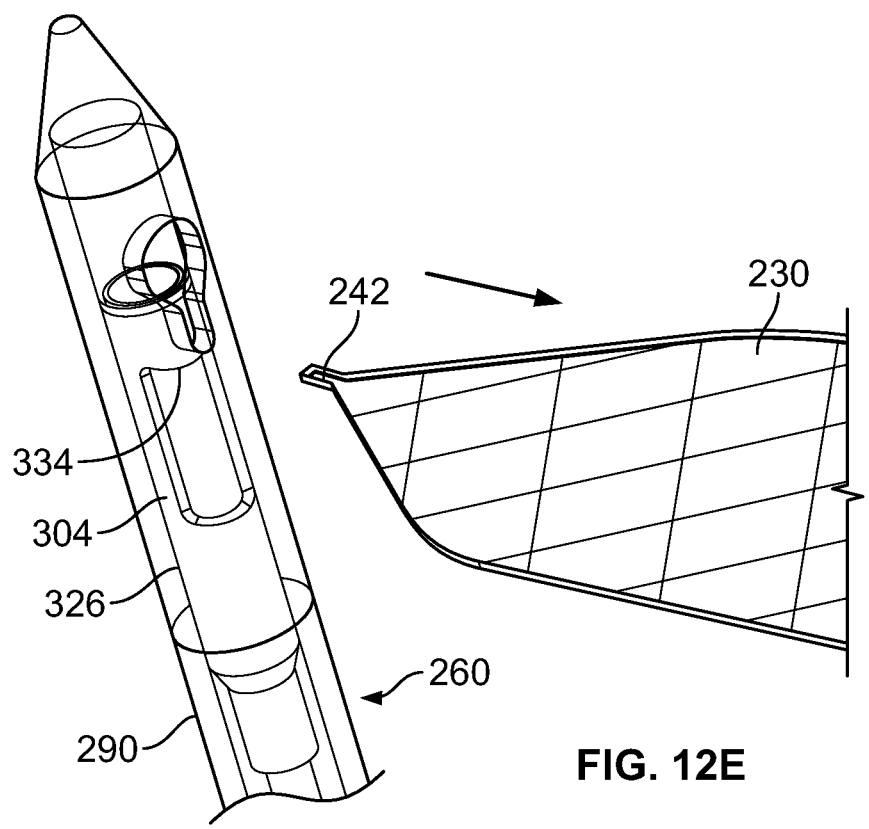
Figure 13A:
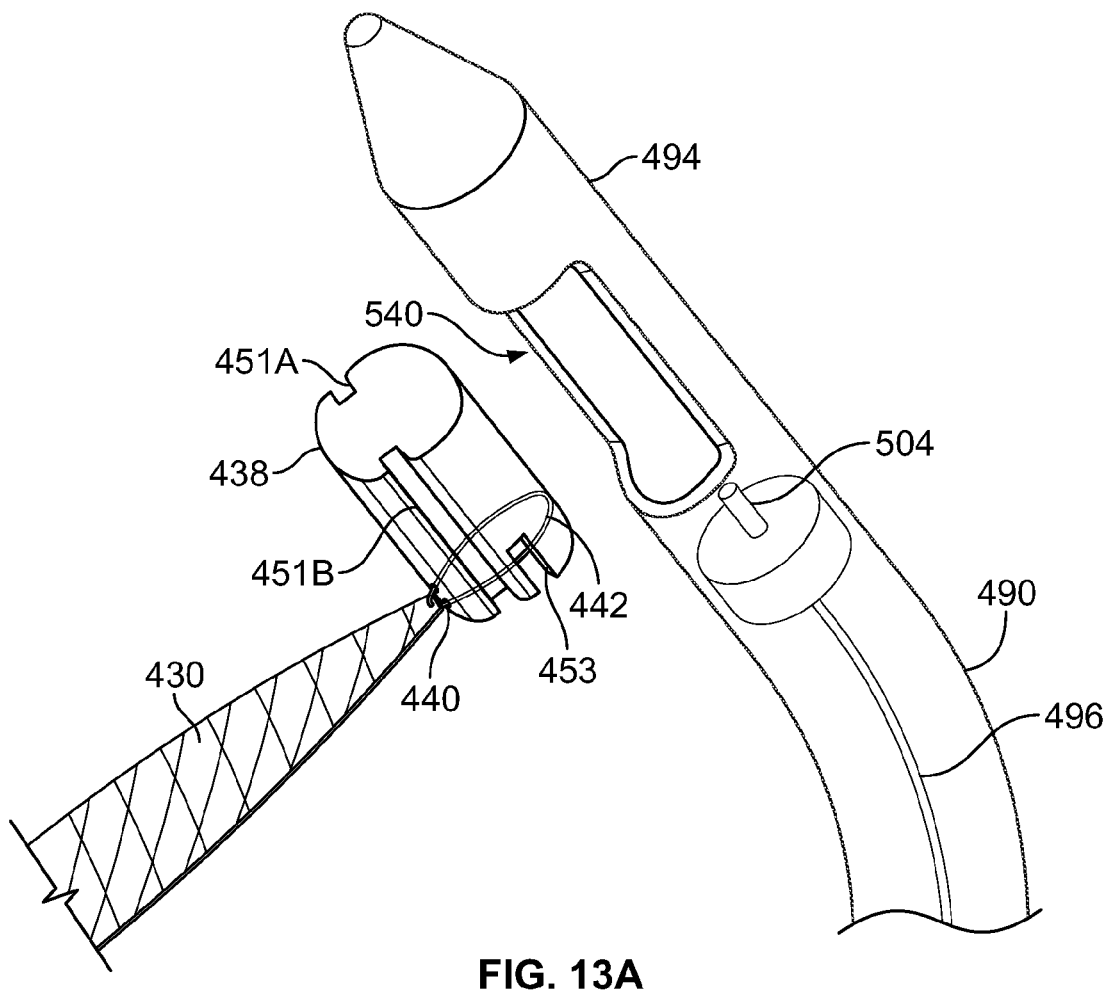
FIG. 13A shows an implant insertion system including a distal end of an elongated shaft of an insertion device and a surgical mesh having an insertion aid connected with an end of the surgical mesh, in accordance with one embodiment of the present invention.
Figure 13B:
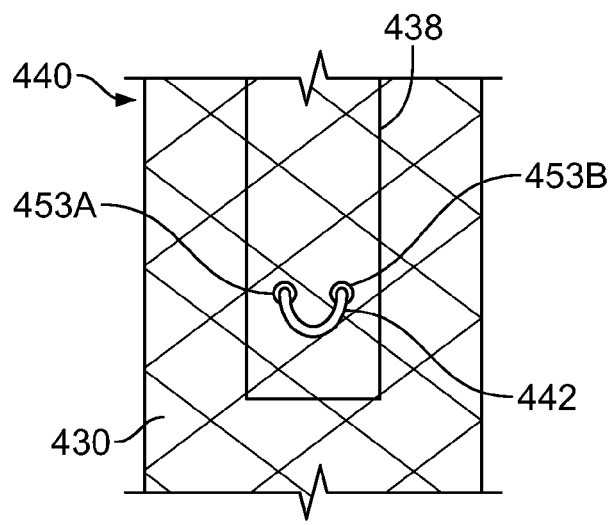
FIG. 13B shown an end view of the insertion aid of FIG. 13A secured to the end of the surgical mesh.

Referring to FIG. 12E, in one embodiment, after the filament 242 has been severed from the insertion aid 238 by the distal cutting edge 334 of the cutting element 304, the surgical mesh 230 is no longer connected with the elongated shaft 290 of the insertion device 260. The severed insertion aid 238 (FIG. 12A) remains within the tubular body 326 of the cutting element 304 for being removed from the tissue when the elongated shaft 290 is retracted from the surgical opening.

Referring to FIGS. 13A-13D, in one embodiment, a surgical mesh 430 has an insertion aid 438 secured to a first end 440 of the mesh using a looped fastener 442. In one embodiment, the insertion aid 438 has a tubular body 445 having a top surface 447, a bottom surface 449, and a pair of aligned grooves 451A, 451B that are formed in the outer wall of the tubular body 445 and that extend along the length of the tubular body 445. The aligned grooves 451A, 451B preferably face away from one another on opposite sides of the tubular body 445. The insertion aid 438 also desirably includes a notch 453 that is formed in the bottom surface 449 of the tubular body 445 and that extends across the face of the bottom surface 449.

In one embodiment, the lower end of the tubular body 445 has a pair of openings 453A, 453B that extend through the tubular body 445. The pair of openings 453A, 453B preferably pass through the notch 453 formed in the bottom surface 449 of the tubular body 445. The looped fastener 442 has a first end secured to the surgical mesh 430 and a second end that is passed through the pair of openings 453A, 453B and the notch 453 for securing the insertion aid 438 to the end of the surgical mesh. The looped fastener 442 may include one or more threads that may be cut or severed for separating the insertion aid 438 from the surgical mesh 430.

Referring to FIGS. 13A-13D, in one embodiment, the insertion aid 438 is coupled with the distal end 494 (FIG. 13A) of an insertion device 460 for implanting the surgical mesh 430 is tissue. In one embodiment, the insertion device includes an elongated shaft 490 having a distal end 494. A lateral opening 540 is formed in the outer wall of the elongated shaft 490. The lateral opening has opposing side walls 541A, 541B that snap fit into the aligned grooves 451A, 451B formed in the tubular body 445 of the insertion aid 438 for securing the insertion aid 438 to the distal end 494 of the elongated shaft 490.

In one embodiment, the insertion device 460 includes a cutting element 504 that may be advanced distally for cutting the looped fastener 442 for severing the insertion aid 438 from its attachment with the surgical mesh 430. When the insertion aid 438 is snap fitted into the lateral opening 540 in the elongated shaft 490, the cutting blade of an advancing cutting element 504 will move into the notch 453 formed in the bottom surface 449 of the tubular body 445 to cut the looped fastener material 442. After the looped fastener material 442 has been cut for severing the insertion aid 438 from the surgical mesh 430, the insertion aid 438 remains snap fitted to the elongated shaft 490 of the insertion device 460, as shown in FIG. 13C, and may be removed from the body when retracting the insertion device 460 from the surgical opening.

Referring to FIG. 14, in one embodiment, a surgical mesh 430' includes an insertion aid 438' having a tubular body 439' with a pair of vertically aligned openings 453A', 453B' that extend through the tubular body 439'. The pair of vertically aligned openings 453A', 453B' preferably pass through a notch formed in the bottom surface 449' of the tubular body, similar to the notch 453 shown in the embodiment of FIG. 13A. A looped fastener 442' may be passed through the pair of vertically aligned openings for securing the insertion aid 438' to the surgical mesh 430'. The looped fastener 442' may be severed by a cutting element of an insertion device disclosed herein for separating the insertion aid from the surgical mesh.

Referring to FIG. 15, in one embodiment, a surgical mesh 430" includes an insertion aid 438" having a tubular body 445" with a pair of diagonally aligned openings 453A", 453B" that extend through the tubular body 445". At least one of the pair of diagonally aligned openings 453A", 453B" preferably passes through a notch formed in the bottom surface 449" of the tubular body 445". A looped fastener 442" may be passed through the pair of diagonally aligned openings 453A", 453B" for securing the insertion aid 438" to the surgical mesh 430". The looped fastener 442" may be severed by a cutting element of an insertion device disclosed herein for separating the insertion aid 438" from the surgical mesh 430".

Figure 16:
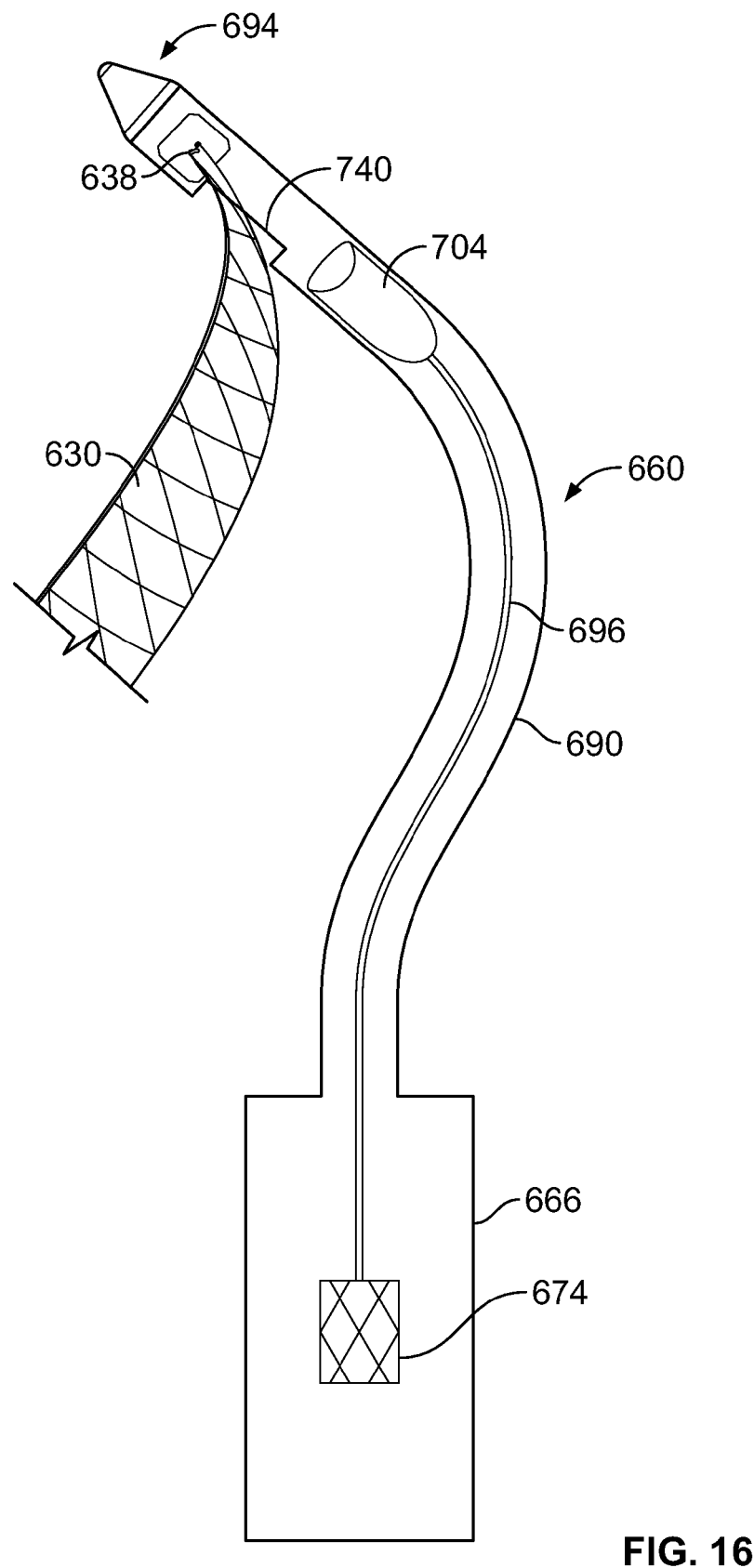
FIG. 16 shows an implant insertion system including a surgical mesh having an insertion aid connected with an end of the surgical mesh and an insertion device, in accordance with one embodiment of the present invention.

Referring to FIG. 16, in one embodiment, an insertion device 660 for a surgical mesh 630 having one or more insertion aids 638 preferably includes a circular or half-moon shaped cutting element 704 for severing a connection between the insertion aid 638 and the surgical mesh 630. In one embodiment, after the insertion aid 638 is secured within an opening 740 at a distal end 694 of an elongated shaft 690, through which an actuating wire 696 extends, on the insertion device 660, the cutting element 704 is advanceable toward the distal end 694 of the elongated shaft 690 for severing the insertion aid 638 from the surgical mesh 630. In one embodiment, the cutting element may move axially, in either a proximal or distal direction for severing an insertion aid. In one embodiment, a cutting element may rotate about an axis for severing an insertion aid.

In one embodiment, an implant insertion system may include a left-hand insertion device and a right-hand insertion device that are essentially mirror images of one another, wherein the left-hand insertion device has a shaft that curves to the left for use on the right side of a patient, and the right-hand insertion device has a shaft that curves to the right for use on the left side of a patient.

In one embodiment, a procedure for inserting an implant in a patient may include placing a patient in a dorsal lithotomy position with the legs flexed about 90 degrees and the tip of the coccyx positioned flush with the edge of a table. The surgical procedure may be carried out under local, regional or general anesthesia. A urethral catheter may be inserted into the patient's bladder for emptying the bladder prior to the procedure.

In one embodiment, using a scalpel, an incision may be made to allow for subsequent passage of an insertion device and an implant. The incision may be used to create a channel that is sufficiently wide for insertion of the implant.

In one embodiment, an implant, such as that shown and described herein, may be removed from a sterile package and positioned on a sterile drape or other suitable sterile location until needed. In one embodiment, a sterile insertion device may be provided and placed upon a sterile drape or other suitable sterile location until needed.

In one embodiment, a sterile guide may be utilized for guiding an insertion device and facilitating insertion of an implant. In one embodiment, the sterile guide may have a marker that is referenced for limiting insertion of the guide.

In one embodiment, a surgeon passes an insertion aid connected with an end of an implant through a keyhole opening provided at a distal end of an elongated shaft of an insertion device. After the insertion device has been secured to the insertion aid of the implant, the guide may be is utilized for properly inserting the insertion tip of the insertion device and the implant into a dissected opening. In one embodiment, a guide for the insertion device may not be utilized.

In one embodiment, the distal end of the elongated shaft and the insertion aid connected therewith are inserted into the dissected tract until the insertion aid reaches a desired location within the tissue.

In one embodiment, the insertion aid is preferably severed from its connection with the implant by engaging an actuator on the handle of the insertion device. As the surgeon engages the actuator, the cutting element at the distal end of the shaft severs the connection between the insertion aid and the end of the implant, whereupon the insertion aid remains disposed within the elongated shaft of the insertion device and the end of the implant has been cut free from being attached to the insertion device. After severing, the elongated shaft of the insertion device may be retracted through the dissected opening.

In one embodiment, an implant may have two or more insertion aids, whereby a first insertion device may be used to sever a first insertion aid from its connection with a first end of the implant, and a second insertion device may be used to sever a second insertion aid from its connection with a second end of the implant. In one embodiment, the surgeon maintains a connection between one of the insertion aids and one of the ends of the implant that provides the best option for final adjustment, if necessary.

In one embodiment, the appropriate tension provided by the implant may be adjusted using an insertion device. The tension may be adjusted to achieve the desired placement for the implant relative to a patient's anatomy. If the tension on the implant is too high, the surgeon may gently move an insertion aid and the implant by slowly retracting the insertion device. After the proper tension level has been obtained, the surgeon preferably cuts the insertion aid from the connection with the end of the implant by engaging the actuator. During cutting, the cutting element may move axially in either a proximal or distal direction, may rotate about the longitudinal axis of the elongated shaft, or may combine rotary and axial movement.

Figure 17:
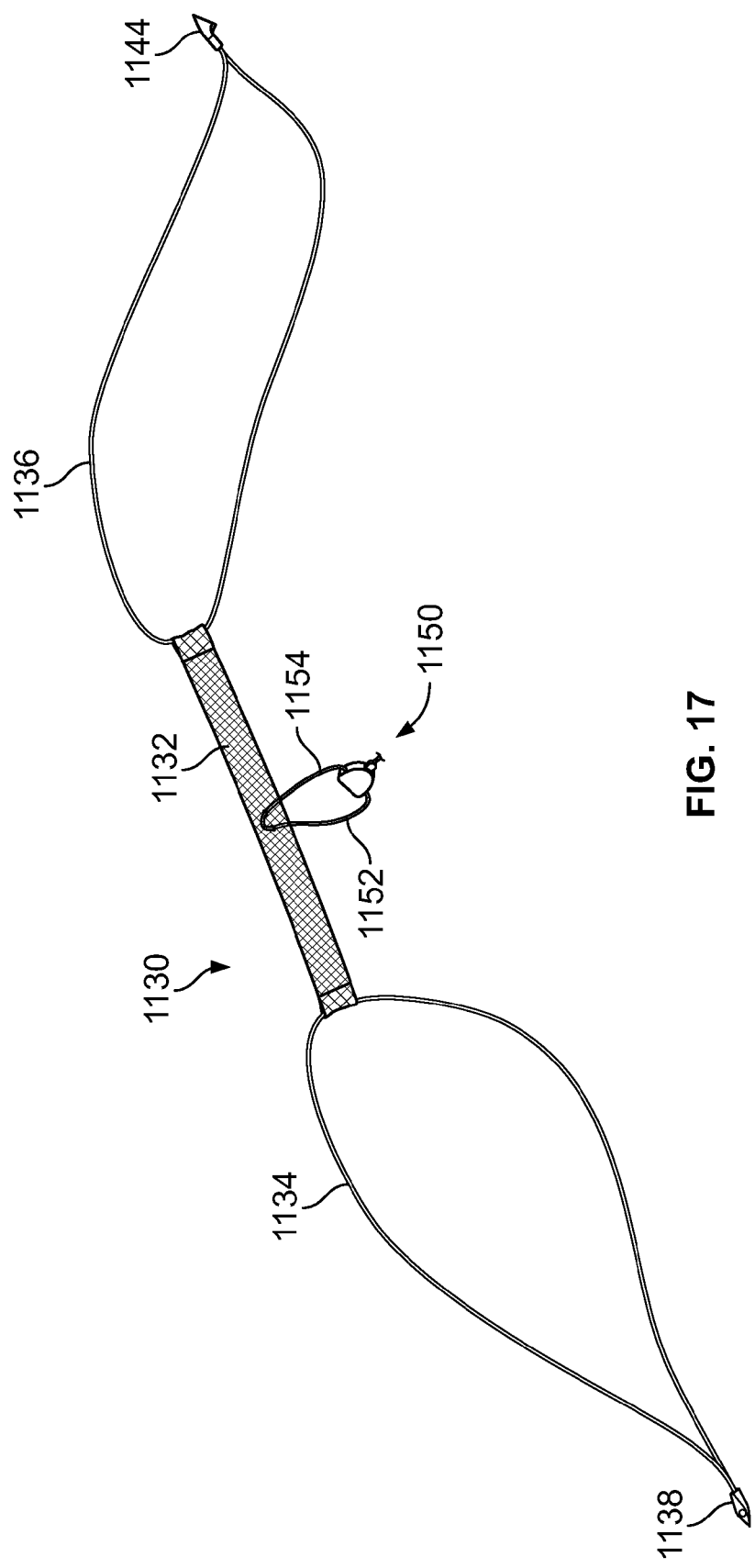
FIG. 17 shows an implant having first and second insertion aids secured to the ends thereof, in accordance with yet another embodiment of the present invention.

Referring to FIG. 17, in one embodiment, an implant 1130 preferably has a central mesh region 1132 and first and second suture loops 1134, 1136 that are connected with and extend from opposite ends of the central mesh region 1132. The implant desirably includes a first insertion aid 1138 that is attached to the outer end of the first suture loop 1134 of the implant, and a second insertion aid 1144 that is attached to the outer end of the second suture loop 1136 of the implant. In one embodiment, filaments, rather than sutures, are used for securing the insertion aids to the ends of the implant. The insertion aids 1138, 1144 are preferably inserted through openings provided at the distal ends of elongated shafts of insertion devices for connecting the suture loops of the implant 1130 with the respective insertion devices for advancing the implant 1130 through tissue to secure the implant 1130 at a desired location within the tissue. In one embodiment, after the implant is positioned in tissue, the insertion aids are severed from the connection with the implant, and the severed insertion aids remain within a shaft of the insertion aid as the insertion aid is retracted from the body.

In one embodiment, plastic sheaths (not shown), such as those used with the Gynecare TVT ABBREVO™ system, may be used to provide for smooth passage of the insertion aids 1138, 1144 and insertion devices through tissue. In one embodiment, the implant 1130 preferably includes an adjustment element 1150 including a loop 1152 attached to the central mesh region 1132 and a gripping button 1154 secured to the loop 1152. In one embodiment, the loop 1152 is a monofilament loop of PROLENE™ suture, and the gripping button 1154 is a polypropylene button. The loop and the button are desirably pre-assembled as part of the implant 1130 at the center of the implant 1130 to aid in the placement of the central mesh region 1132 of the implant 1130 under a urethra.

Figure 18:
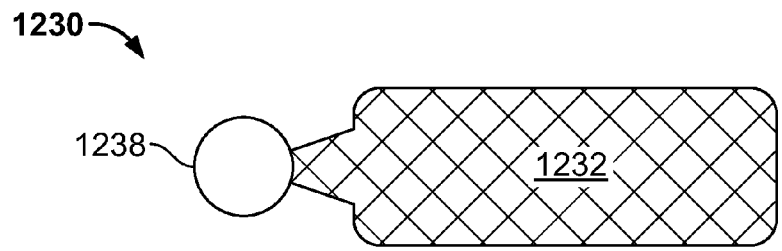
FIG. 18 shows an implant having a single insertion aid, in accordance with one embodiment of the present invention.

Referring to FIG. 18, in one embodiment, an implant 1230 includes a surgical mesh 1232 having a single insertion aid 1238 connected to an end of the surgical mesh 1232. The insertion aid 1238 may be severed from its connection to the surgical mesh 1232 using the insertion tools disclosed herein.

Figure 19:
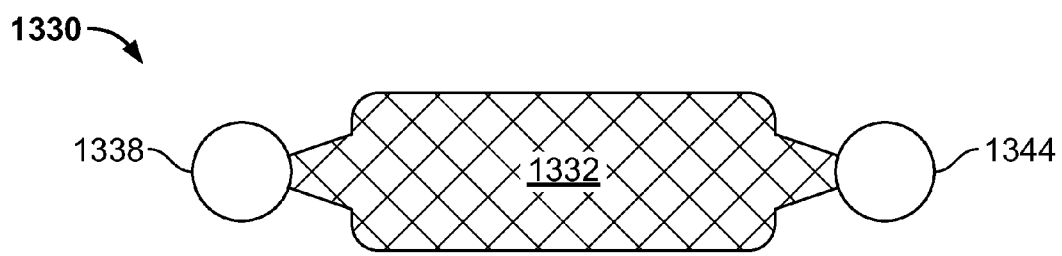
FIG. 19 shows an implant having two insertion aids, in accordance with one embodiment of the present invention.

Referring to FIG. 19, in one embodiment, an implant 1330 includes a surgical mesh 1332 having a first insertion aid 1338 connected to a first end of the surgical mesh 1332 and a second insertion aid 1344 connected to a second end of the surgical mesh 1332. The insertion aids 1338, 1344 may be severed from their connections to the surgical mesh 1332 using the insertion tools disclosed herein.

Figure 20:
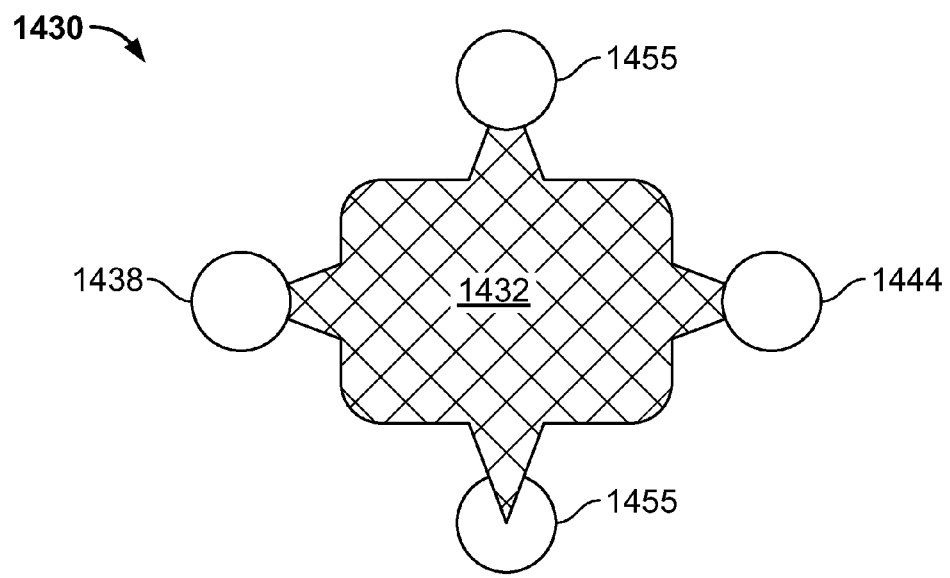
FIG. 20 shows an implant having four insertion aids, in accordance with one embodiment of the present invention.

Referring to FIG. 20, in one embodiment, an implant 1430 includes a mesh or pad 1432 having four insertion aids 1438, 144, 1445, and 1455 connected to different sections of the mesh or pad. The insertion aids 1438, 1444, 1445, and 1455 may be severed from their connections to the surgical mesh 1432 using the insertion tools disclosed herein. Although four insertion aids are shown in the embodiment of FIG. 20, other embodiments may have five or more insertion aids connected with the implant.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An implant insertion system comprising:
an implant having an end;
at least one insertion aid connected with said end of said implant;
an insertion device including a handle, an actuator, an elongated shaft extending from said handle, an actuating wire disposed within said elongated shaft and configured to move in proximal and distal directions relative to said elongated shaft, and a cutting element disposed within said elongated shaft, said cutting element being connected with a distal end of said actuating wire and said actuator being connected with a proximal end of said actuating wire, said elongated shaft having an outer wall including an opening that is configured to receive said at least one insertion aid for connecting said implant with said insertion device, wherein said actuator is pushed toward a distal end of said elongated shaft for moving said cutting element from a first position to a second position for breaking a connection between said at least one insertion aid and said implant.

2. The implant insertion system as claimed in claim 1, wherein said implant comprises:
a surgical mesh having a first end and a second end;
a first insertion aid connected with said first end of said surgical mesh; and
a second insertion aid connected with said second end of said surgical mesh.

3. The implant insertion system as claimed in claim 2, wherein said surgical mesh comprises a first material and said first and said second insertion aids comprise a second material that is different than said first material.

4. The implant insertion system as claimed in claim 2, further comprising a first link connecting said first insertion aid with said first end of said surgical mesh and a second link connecting said second insertion aid with said second end of said surgical mesh.

5. The implant insertion system as claimed in claim 4, wherein said first and second links comprise threads that pass through pores of said surgical mesh and are wrapped around said first and second insertion aids.

6. The implant insertion system as claimed in claim 4, wherein said cutting element contacts said first link and said second link when moving between the first and the second positions for separating said first and second insertion aids from said surgical mesh.

7. The implant insertion system as claimed in claim 6, wherein said opening in said outer wall is located at a distal end of said elongated shaft.

8. The implant insertion system as claimed in claim 7, wherein said opening at the distal end of said elongated shaft has a keyhole shape defining a keyhole opening with a wider distal section and a narrower proximal section.

9. The implant insertion system as claimed in claim 8, wherein said at least one insertion aid has a diameter that is smaller than a size of said wider distal section of said keyhole opening and larger than a size of said narrower proximal section of said keyhole opening.

10. The implant insertion system as claimed in claim 1, wherein said at least one insertion aid has geometric shapes selected from the group consisting of spheres, circles, squares, rectangles, tubes, cubes and parallelograms.

11. The implant insertion system as claimed in claim 1, wherein said cutting element has a distal end with a pointed tip.

12. The implant insertion system as claimed in claim 11, wherein said pointed tip projects beyond a distal end of said elongated shaft when said cutting element is in the first position and is proximal to the distal end of said elongated shaft when said cutting element is in the second position.

13. The implant insertion system as claimed in claim 1, wherein said insertion device further comprising a pointed tip at a distal-most end of said elongated shaft.

14. The implant insertion system as claimed in claim 1, wherein said elongated shaft has an elongated conduit extending from a proximal end to the distal end of said elongated shaft, and wherein said actuating wire is disposed within said elongated conduit of said elongated shaft.

15. An implant insertion system comprising:
an implant having a first end and a second end;
a first insertion aid spaced from and connected with said first end of said implant via a first link;
a second insertion aid spaced from and connected with said second end of said implant via a second link;
an insertion device for implanting said implant in tissue, said insertion device including a handle at a proximal end thereof, an actuator mounted on said handle, a shaft extending from a distal end of said handle toward a distal end of said insertion device, and a cutting element disposed within said shaft, said shaft having an outer wall including an opening that is configured to receive said first and second insertion aids for connecting said implant with said insertion device, wherein said actuator is engageable for moving said cutting element from a first position to a second position for severing one of said links for breaking a connection between one of said first and said second insertion aids and said surgical implant;
wherein said insertion device further comprises said shaft having an elongated conduit extending from a proximal end to a distal end of said shaft, an actuating wire disposed within said elongated conduit of said shaft and configured to move in proximal and distal directions relative to said shaft, said cutting element being connected with a distal end of said actuating wire, and said actuator being connected with a proximal end of said actuating wire, wherein said actuator is pushed toward the distal end of said shaft for moving said cutting element between the first position and the second position.

16. The implant insertion system as claimed in claim 15, wherein said insertion device has a longitudinal axis, and wherein said cutting element disposed within said shaft moves along the longitudinal axis of said insertion device between said first position and said second position.

17. The implant insertion system as claimed in claim 15, wherein said cutting element comprises a straight cutting edge.

18. The implant insertion system as claimed in claim 15, wherein said cutting element comprises a tubular body having a proximal end connected with the distal end of said actuating wire, said tubular body having a window formed in an outer wall thereof that is in axial alignment with said opening in said outer wall of said shaft when said cutting element is in the first position and is not in alignment with said opening in said outer wall of said shaft when said cutting element is in the second position.

19. The implant insertion system as claimed in claim 18, wherein when said cutting element is in the first position, one of said first and said second insertion aids is insertable through said opening in said outer wall of said shaft and said window formed in said tubular body of said cutting element.

20. The implant insertion system as claimed in claim 15, wherein said shaft comprises metal, said cutting element comprises metal, said handle comprises a polymer material, said implant comprises mesh or a mesh and suture combination, said first and said second insertion aids comprise a polymer, and said actuating wire is flexible and is selected from the group of materials consisting of stainless steel, polymers, nylon, Teflon, polypropylene and combinations thereof.

21. The implant insertion system as claimed in claim 15, wherein said insertion aids are severed from said implant by moving said actuator toward a distal end of said handle, which, in turn, rotates a cam mounted within said handle in a counterclockwise direction, which, in turn, pulls said actuating wire proximally for moving said cutting element proximally from the first position to the second position.

22. The implant insertion system as claimed in claim 15, wherein said insertion device comprises a left-hand insertion device for engaging said first insertion aid and a right-hand insertion device for engaging said second insertion aid.

23. An implant insertion system comprising:
an implant having a first end and a second end;
a first insertion aid spaced from and connected with said first end of said implant via a first link;
a second insertion aid spaced from and connected with said second end of said implant via a second link;
an insertion device for implanting said implant in tissue, said insertion device including a handle at a proximal end thereof, an actuator mounted on said handle, a shaft extending from a distal end of said handle toward a distal end of said insertion device, an actuating wire disposed within said shaft and configured to move in proximal and distal directions relative to said shaft, and a cutting element disposed within said shaft, said cutting element being connected with a distal end of said actuating wire and said actuator being connected with a proximal end of said actuating wire, said shaft having an outer wall including an opening that is configured to receive said first and second insertion aids for connecting said implant with said insertion device, wherein said insertion aids are severed from said implant by moving said actuator toward said distal end of said handle, which, in turn, rotates a cam mounted within said handle in a counterclockwise direction, which, in turn, pulls said actuating wire proximally for moving said cutting element proximally from a first position to a second position.

24. The implant insertion system as claimed in claim 23, wherein said cutting element comprises a tubular body having a proximal end connected with the distal end of said actuating wire, said tubular body having a window formed in an outer wall thereof that is in axial alignment with said opening in said outer wall of said shaft when said cutting element is in the first position and is not in alignment with said opening in said outer wall of said shaft when said cutting element is in the second position.

25. The implant insertion system as claimed in claim 23, wherein said insertion device comprises a left-hand insertion device for engaging said first insertion aid and a right-hand insertion device for engaging said second insertion aid.

* * * * *